United States Patent [19]
Allington

[11] Patent Number: 5,843,294
[45] Date of Patent: Dec. 1, 1998

[54] CAPILLARY ELECTROPHORESIS SAMPLE INJECTION TECHNIQUE

[75] Inventor: Robert William Allington, Lincoln, Nebr.

[73] Assignee: Isco, Inc., Lincoln, Nebr.

[21] Appl. No.: 592,833

[22] Filed: Oct. 4, 1990

Related U.S. Application Data

[63] Continuation-in-part of Ser. No. 469,311, Jan. 24, 1990, Pat. No. 5,169,511, which is a continuation-in-part of Ser. No. 277,566, Nov. 29, 1988, Pat. No. 5,354,440.

[51] Int. Cl.[6] .................... G01N 27/26; G01N 27/447
[52] U.S. Cl. ............................. 204/453; 204/604
[58] Field of Search ................. 204/299 R, 180.1

[56] References Cited
U.S. PATENT DOCUMENTS 5,207,886  5/1993  Lauer et al. ................ 204/299 R

FOREIGN PATENT DOCUMENTS

| 329341 | 8/1989 | European Pat. Off. | 204/299 R |
| 339779 | 11/1989 | European Pat. Off. | 204/299 R |
| 339781 | 11/1989 | European Pat. Off. | 204/299 R |

*Primary Examiner*—Robert J. Warden
*Assistant Examiner*—John S. Starsiak, Jr.
*Attorney, Agent, or Firm*—Vincent L. Carney

[57] ABSTRACT

To inject sample into a capillary tube of an electrophoresis apparatus, a vacuum tank is connected to one end of the tube while the other end is in sample to impart a pressure difference across the tube. The pressure in the pressure chamber is sensed, integrated and used to determine and control the amount of sample drawn and to correct peak data.

44 Claims, 12 Drawing Sheets

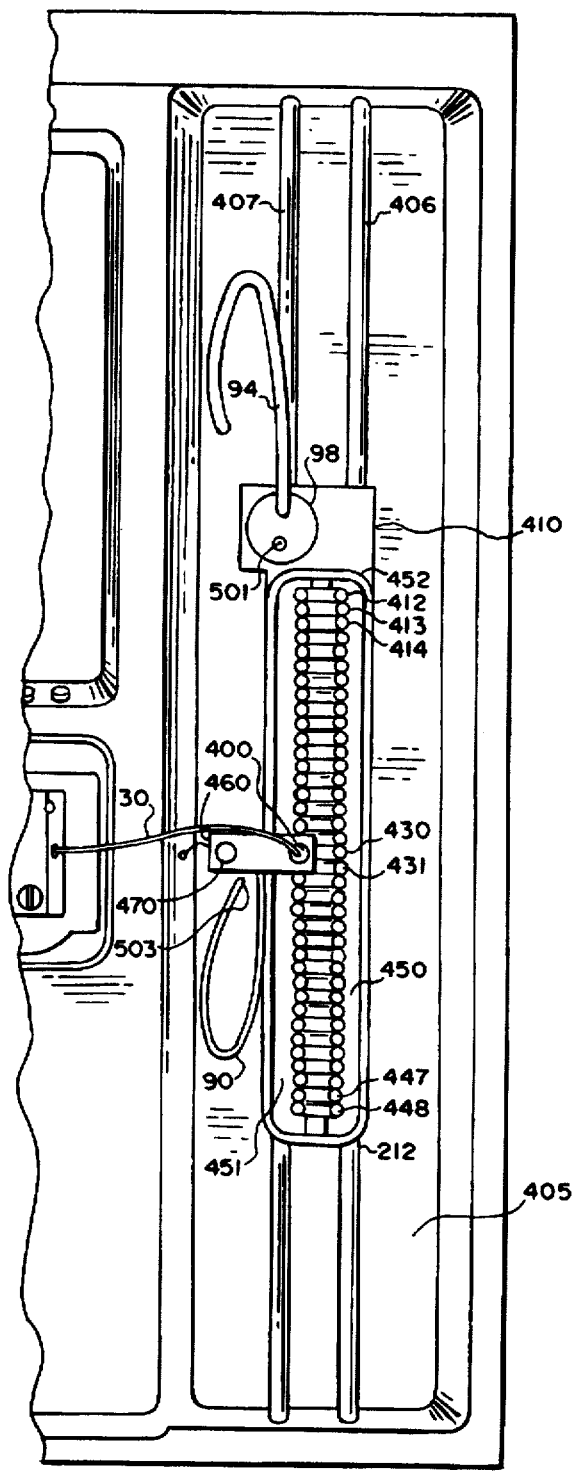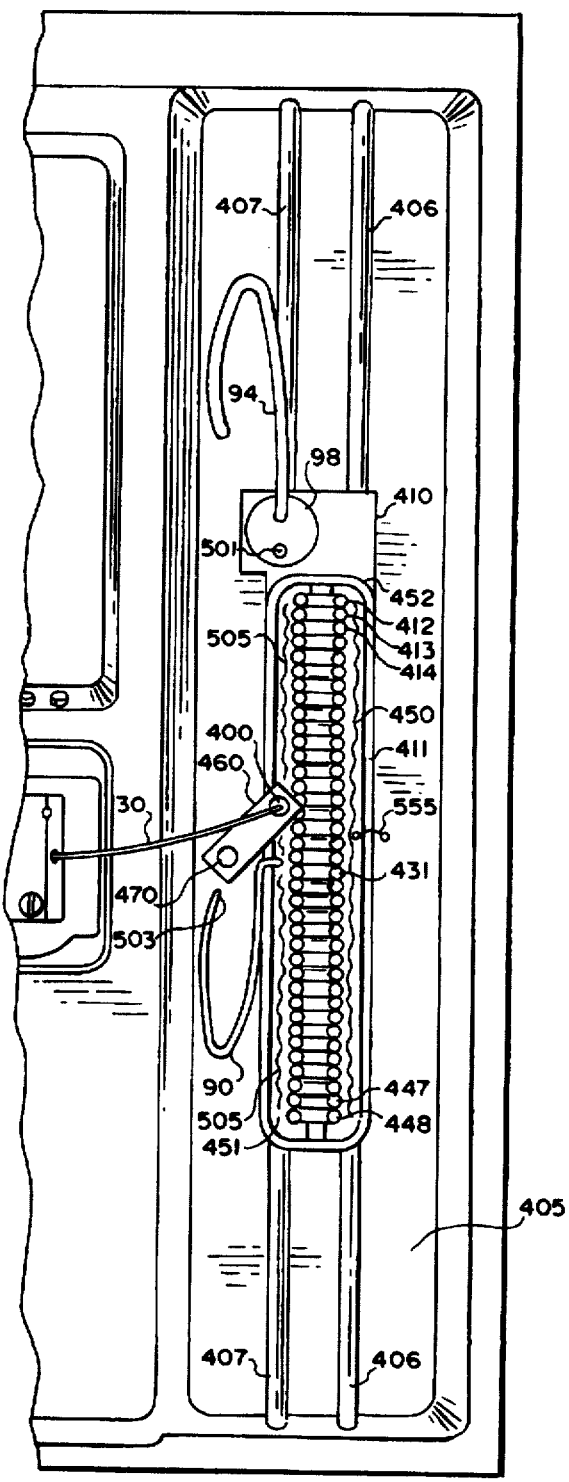

CAPILLARY ELECTROPHORESIS SAMPLE INJECTION TECHNIQUE

RELATED CASES

This application is a continuation-in-part of U.S. application Ser. No. 07/469,311 filed Jan. 24, 1990, now U.S. Pat. No. 5,169,511 which is a continuation in part of application Ser. No. 277,566 filed Nov. 29, 1988, now U.S. Pat. No. 5,354,440 in the name of Robert William Allington and assigned to the same assignee as this application.

BACKGROUND OF THE INVENTION

This invention relates to techniques in the separation sciences and more particularly to techniques for introduction of sample specimen to be separated, such as for example, sample to be separated by capillary electrophoresis.

It is known in the separation sciences to automatically introduce sample into a separating apparatus. One type of such separating apparatus performs separation by electrophoresis and is known as an electrophoresis apparatus. In this process, the samples are separated in a medium as the molecular species are moved through the medium under the influence of an electrical potential.

One class of electrophoresis apparatus is a capillary electrophoresis apparatus. In a capillary electrophoresis apparatus, the medium is in a small diameter capillary tube. This tube is usually made of fused quartz. The electrophoresis medium may be a gel or liquid in capillary electrophoresis. The separated bands or zones of molecular species are sensed by a detector that transmits light through the medium and senses the species as they move along the medium by differences in absorbance of the light. The volume of sample to be injected is low, such as for example, 2 nanoliters.

Sample injection valves have been used for introducing samples into separating devices such as liquid chromatography. However, such prior art sample injectors are not easily used with capillary electrophoresis apparatuses because of the small sample volume required.

A prior art technique for sample injection usable with capillary liquid chromatography is to electrophorese or electromigrate a portion of sample into the end of the capillary tube. This has the disadvantage of producing a quantitative bias toward sample components of higher electrophoretic mobility. Another prior art technique is to use a pressure difference to draw sample into the capillary for a preset, measured period of time. The pressure difference is usually created by a vacuum or by locating the outlet of the capillary in a buffer vessel at a lower elevation than the sample-containing vessel at the inlet end of the capillary. Although this is a popular method of sample injection, its accuracy in capillary electrophoresis falls short of accuracy common with other separation methods, such as using a sample injection valve with high performance liquid chromatography. The word "accuracy" as used herein especially includes repeatability.

SUMMARY OF THE INVENTION

Accordingly, it is an object of the invention to provide novel techniques for use in the separation sciences.

It is a further object of the invention to provide a novel sample injector in the separation sciences.

It is a still further object of the invention to provide a novel sample injector suitable for use in introducing samples into capillary separation equipment such as capillary electrophoresis and capillary liquid chromatography.

It is a still further object of the invention to provide a novel technique for introducing very small volumes of liquid sample with good repeatability, precision, and setability in physical units.

It is a still further object of the invention to provide a technique for improving sample injection accuracy by integrating the injection pressure during the period of injection.

In accordance with the above and further objects of the invention, a capillary electrophoresis apparatus includes a capillary tube, means for injecting samples into the tube, means for applying a potential across the tube and a fraction collector adapted to receive fractions of one or more zones detected by the electrophoresis apparatus in separate containers, with the source of potential being adapted to be applied to the end of the tube within the different containers of the fraction collector.

The means for injecting samples into the tube includes a pressure chamber, means for causing pressure in said pressure chamber to inject sample from said source of sample at a slow rate into an end of the capillary tube, pressure measuring means adapted to measure the pressure in said chamber and generate a signal indicative thereof and means for causing an increase in the accuracy of quantative results obtained from said sample in response to said signal.

The pressure chamber communicates with a first end of the capillary tube to impart a pressure difference with respect to the opposite end of the capillary tube which opposite end is adapted to communicate with a sample source. The flow in the capillary tube is proportional to the pressure difference and the means for causing an increase in accuracy incorporates correction means which integrates the pressure differences with respect to time and uses the integral to correct or normalize data to compensate for different sizes of sample that may be introduced.

In a first embodiment, the vacuum in the pressure vessel is applied to inject sample and simultaneously the accumulating integral is monitored. When the integral reaches a preset value, the vacuum is disconnected and the pressure vessel is vented to atmosphere. This embodiment has an advantage in that the sample volume may be preset in terms of real pressure multiplied by time units, such as kiloPascal-seconds.

In a second embodiment, which is a refinement of the first embodiment, the pressure vessel is disconnected from the vacuum pump and vented to atmosphere when the accumulated integral reaches the preset value. The integral continues to accumulate past the preset value to a final value. These two integrals of the reduction in negative pressure with respect to the time of sample injection, namely the integral to the preset value and the integral after the preset value, are used to correct peak data. Peak data are corrected by multiplying them by the preset integral value and then dividing them by the final integral of the negative pressure reduction.

A third embodiment is a refinement of the first embodiment in which a calibrating or dummy sample is drawn in the same manner as in the second embodiment. The accumulating integral is measured and the vacuum disconnected upon reaching a preset value of the integral, but the final value of the integral is also measured up to pressure equilibrium, which is at atmospheric pressure. The difference between the preset integral and the final value of the integral represents an error that is corrected by subtracting this error from the preset value to form a corrected preset value. This process may be repeated at each sample drawing.

From the above description, it can be understood that the electrophoresis apparatus of this invention has the advantage of permitting rapid, repeatable accurate sample injection.

SUMMARY OF THE DRAWINGS

The above noted and other features of the invention will be better understood from the following detailed description when considered with reference to the accompanying drawings, in which:

FIG. 13 is an enlarged fragmentary plan view of a portion of the fraction collector of FIG. 1;

FIG. 14 is an enlarged fragmentary plan view of a portion of the fraction collector of FIG. 1;

DETAILED DESCRIPTION

Figure 1:
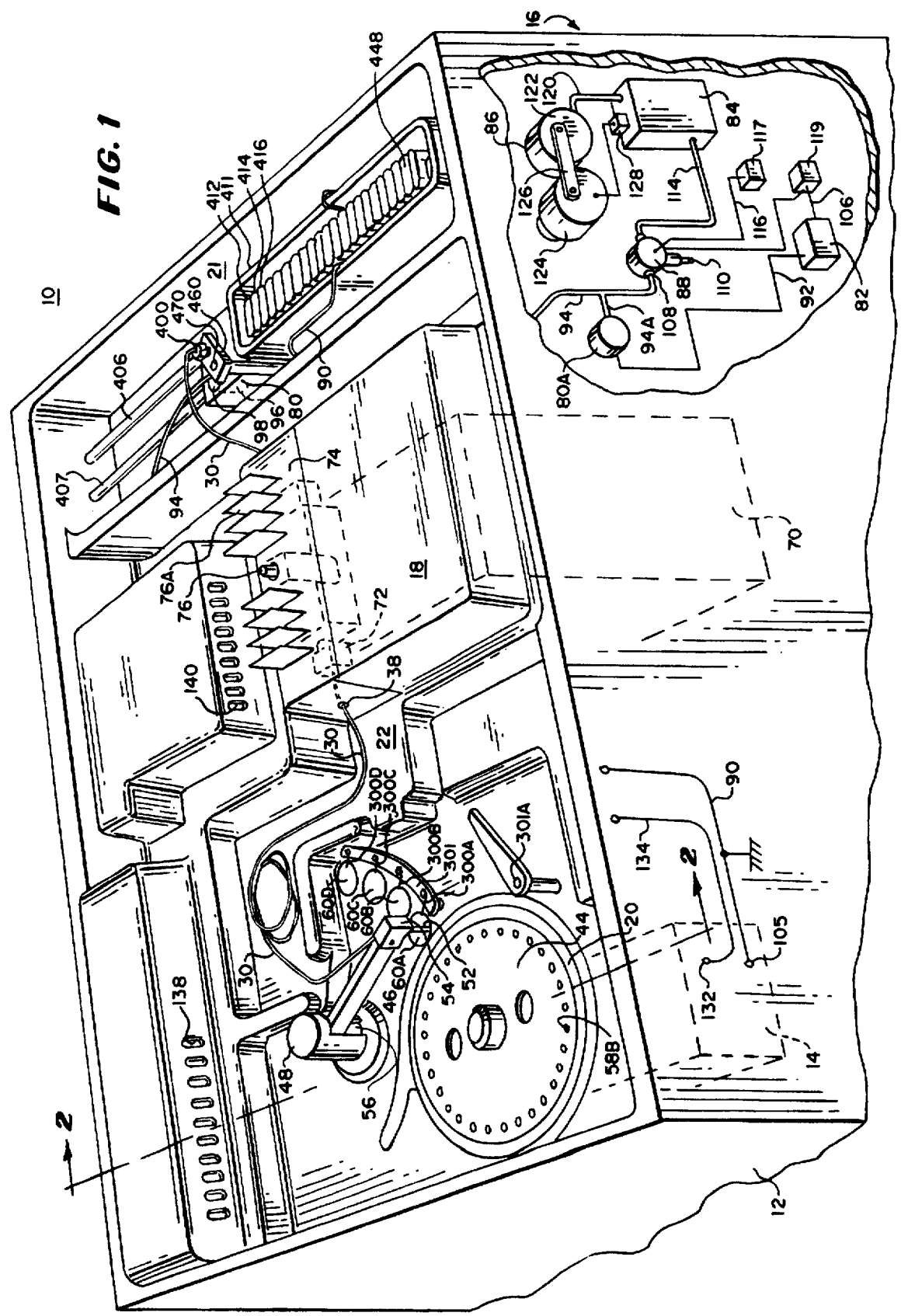
FIG. 1 is a simplified perspective view of an electrophoresis apparatus according to the invention including a sample injection mechanism.

In FIG. 1, there is shown a capillary electrophoresis apparatus 10 having a cabinet 12, power supply 14, a sample injection system 16, a sensing section 18, a sample changing system 20, an electrophoresis section 22 and a fraction collector system 21. This capillary electrophoresis apparatus is similar to the apparatus 10 disclosed in U.S. application Ser. No. 277,566 filed Nov. 29, 1988, now U.S. Pat. No. 5,354,440 in the name of Robert William Allington and assigned to the same assignee as this application but includes a fraction collector section 21. The cabinet 12 is shown in FIG. 1 with its top removed. It supports the power supply 14, the sample changing system 20, the electrophoresis section 22, the sensing section 18, the sample injection system 16 and the fraction collector system 21 which are connected together to separate molecular species.

The electrophoresis section 22 is connected to the sample changing system 20 and adapted for maintaining at least one portion of the electrophoretic separating region of the capillary tube horizontal. The sensing section 18 is connected to the electrophoresis section 22 and includes a light absorbance detection cell for monitoring the separation, and is an improved way of introducing a precise sample volume to be described hereinafter. The fraction collector section 21 includes a plurality of sample collection cells 412–448, carrier 411, electrodes and a drive mechanism. The sample cups are adapted to receive separated molecular species.

To remove the carrier 411 and deposit effluent in individual cells, the sample injection system 16 and fraction collection mechanism 21 includes carrier 411 and the controllable-pressure vessel 80 with cap 98. The carrier 411 and controllable-pressure vessel are supported on a support plate 410 (FIG. 7) which moves slideably, horizontally on guide rails 406 and 407. A capillary tube 30 may be led through removable cap 98 which covers the controllable-pressure vessel 80 under the cap 98. The vessel 80 is mounted in a recess in support plate 410 (FIG. 7) and moves with carrier 411.

Sealing piece 400A (FIG. 7) is in the shape of a frustum of a cone and makes a seal with conical hole 501 (FIG. 13) in cap 98 when a arm is lowered. The vessel 80 may have a vacuum applied to it through flexible connecting tubing 94 for initially filling the capillary tube 30 with electrolyte and for loading sample into the capillary tube 30. Flexible connecting tubing 94 is led through hole 502 (FIGS. 13 and 14) in mounting surface 405 to the sample injection system pressure control system 16. A liquid trap 503 (FIG. 22) is located on connecting tubing 94 under surface 405. This trap must produce negative resistance air flow in connecting tubing 94.

The pressure control part of the sample injection system 16 is located under mounting surface 405. When operating, the injection apparatus establishes a negative pressure in the vessel 80 under cap 98 which pulls filling buffer into the capillary tube 30 from one of the buffer beakers 60A, 60B, 60C or 60D; or a small amount of sample from one of the sample vessels located on sample changing system 20 in a manner similar to that disclosed more completely in U.S. application Ser. No. 07/277,566 now U.S. Pat. No. 5,354,440 filed in the name of Robert W. Allington and assigned to the same assignee as this application; and in U.S. application Ser. No. 07/469,311, now U.S. Pat. No. 5,169,511 filed in the name of Robert W. Allington et al. and assigned to the same assignee, the disclosures of which are incorporated by reference herein.

Figure 7:
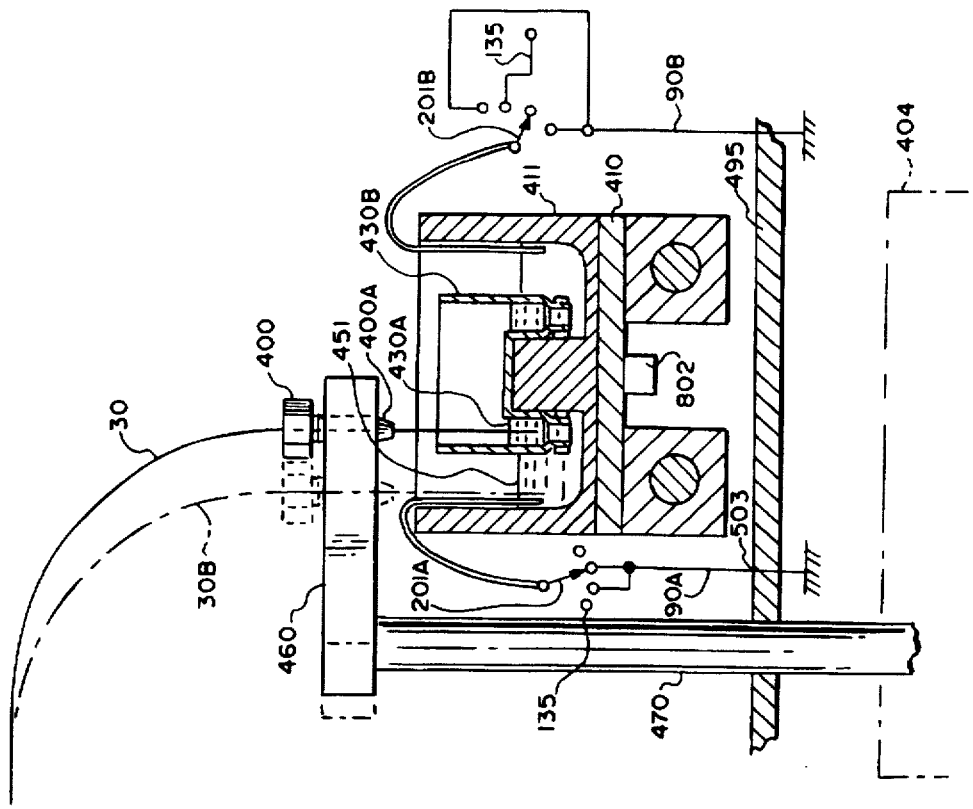
FIG. 7 is a cross sectional view of the fraction collecting mechanism of FIG. 1 indicating part of its operating cycle.

The carrier 411 holds a number of sample collection cells 412 through 448 (FIG. 13). Carrier 411 is equipped with a grounding electrode 505 (FIG. 7) which is immersed in conducting electrolyte 451 (FIG. 7). Electrode 505 (FIG. 7) is connected by flexible conductor 90 and is led through hole 503 (FIG. 7) in mounting surface 405 to the electrical ground connected to terminal 105 of the high voltage power supply 14 in FIG. 1. Carrier 411 also has electrode 555 (FIG. 14) which is immersed into conductivity electrolyte 450 (FIG. 7).

With this arrangement, the sample changing system 20 causes one end of the capillary tube 30 to contact a sample and the sample injection system 16 pulls sample into the end and causes one end of the capillary tube 30 to be in contact with a buffer at a potential suitable for electrophoresis. Power is applied at a high potential while the sample is within the part of the capillary tube 30 which is horizontal to rapidly electrophores the sample with low diffusion. The separated bands are sensed and collected by: (1) transmitting light through narrow slits on opposite sides of the separating medium in the sensor; (2) determining the absorbance of the bands; and (3) collecting the bands in sample cells that are moved into position to receive one or more or a part of one of the sensed bands in response to signals from the sensor.

Figure 3:
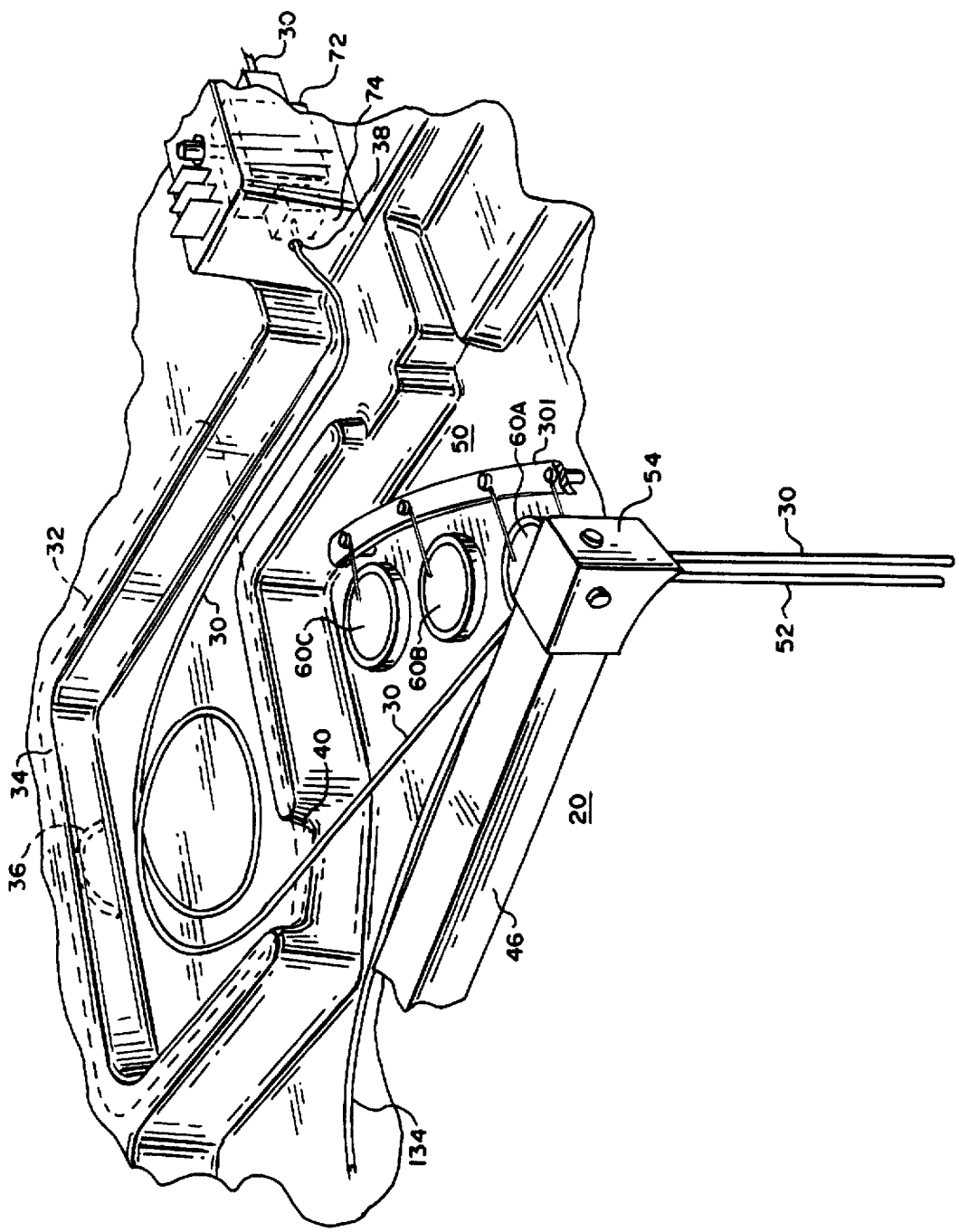
FIG. 3 is a simplified fragmentary perspective view of a portion of the apparatus of FIG. 2.

In the preferred embodiment, the sample changing system 20 inserts one end of the capillary tube 30 into a sample, and after the sample injection system 16 has pulled sample into the end, the sample changing system 20 inserts the end of the capillary tube 30 into a buffer from an electrolyte section 50 (FIG. 3). Power is applied and, when the sample is in a horizontal portion of the capillary tube, the voltage is increased to speed the separation.

In some embodiments, the capillary tube 30 is horizontal throughout its length of electrophoresis and the sample changer need not move the end of the capillary tube 30 from the sample to the buffer. In this embodiment, the horizontal capillary tube that contains sample is inserted horizontally into the buffer by means of some suitable method, such as piercing a resealable container. In another embodiment, the sample containers and buffer are moved into contact with the end of the capillary tube 30 rather than moving the end of the capillary tube 30.

The electrophoresis section 22 is located within the cabinet 12 for temperature control during electrophoresis and includes a capillary tube 30, a removable horizontal cover plate 32 (FIG. 3) and a horizontal ledge 34 (FIG. 3), which cover plate 32 (FIG. 3) rests on the horizontal ledge 34 (FIG. 3) in the cabinet 12. The removable horizontal cover plate 32 (FIG. 3) and horizontal ledge 34 (FIG. 3) contain the capillary tube 30 between them within a recess in the horizontal ledge 34 (FIG. 3) shaped to permit a change in the length of the capillary tube 30 between the removable horizontal cover plate 32 (FIG. 3) and horizontal ledge 34 (FIG. 3). This permits the movement of the end of the capillary tube 30 by a sample changer while the capillary tube 30 is maintained in a horizontal position even though the distance between the sample changer and the light sensor changes.

The capillary tube 30 has: (1) a first end that extends from the electrophoresis section 22 into the sample changing system 20 where it is held for contact with the sample and buffer, which may be by movement into the sample and buffer solution; (2) a central section within the electrophoresis section 22 which is preferably horizontal and through which electrophoresis takes place under some circumstances at high voltage; and (3) a second end section that extends from the electrophoresis section 22 into the sensing section 18, the sample injection system 16 and the fraction collecting system 21.

The capillary tube 30 is made of quartz in the preferred embodiment with an inside diameter of between 0.005 and 0.5 millimeter and may include any separating medium. The capillary tube wall in the preferred embodiment is in the thickness range of between 0.1 and 0.2 millimeters. Its length may be from 5 to 500 centimeters. While a capillary tube of the conventional type for electrophoresis is contemplated for the preferred embodiment, other sizes of tubes and tubes of other materials may obviously be used.

To provide temperature control by cooling the horizontal section of capillary tube 30 within the elongated horizontal recess in ledge 34 (FIG. 3), the horizontal ledge 34 (FIG. 3) and removable horizontal cover plate 32 (shown in phantom in FIG. 3) are preferably made of highly thermally conductive material-and/or the removable horizontal cover plate 32 includes extensive perforations to facilitate cooling of the capillary tube 30. The removable horizontal cover plate 32 may be removed with handle 36 (FIG. 3).

To permit the capillary tube 30 to extend beyond the elongated recess and the horizontal ledge 34 to the sample changing system 20 and the sensing section 18: (1) a notch 40 is provided at one side (the left end as viewed in FIG. 3) in horizontal ledge 34 to receive the capillary tube 30 from the sample changing system 20; and (2) another notch is provided in the other end, which is the right end as viewed in FIG. 3, to permit the capillary tube 30 to pass out of the electrophoresis section 22 through hole 38 (FIG. 3) in the sensing section 18.

To supply samples to the capillary tube 30, the sample changing system 20 includes a sample holding reel 44, a movable arm 46, a rotor head 48 and an electrolyte section 50 (FIG. 3). The sample holding reel 44 and electrolyte section 50 contain sample and electrolyte in spaced apart containers. The movable arm 46 is carried by the rotor head 48 and is movable in two directions to insert an electrode 32 in the electrolyte and the end of the capillary tube 30 into the electrolyte and sample.

This electrode 52 and the capillary tube 30 are mounted by a bracket 54 to the movable arm 46 of the sample changing system 20. The bracket 54 mounts the capillary tube 30 at a horizontal level that is, when the end capillary tube is lowered into contact with the electrolyte, the same as the level of the recess in the horizontal cover plate 34 and the level of a sensor 72 (FIG. 3) to maximize the length that is horizontal. In one embodiment, the arm 46 moves up and down through slot 56 in rotor head 48 of the sample changing system 20.

In another embodiment, the arm 46 and its shaft move up and down and rotate and the rotor casing is not necessary. This enables dipping the capillary tube 30 in sample vials indicated as 58A, 58B, (etc.) in the removable sample holding reel 44. The removable sample holding reel 44 is programmably rotatable to bring any of its 40 sample tubes under capillary tube 30 and rotor head 48 is rotatable to place the capillary tube 30 either over a sample tube or over electrolyte vessels 60A, 60B, 60C or 60D in the electrolyte section 50 (FIG. 3).

When the desired electrolyte vessel or a sample tube is selected by rotation of rotor head 48, movable arm 46 moves downward to put the end of capillary tube 30 either in contact with the sample in the sample tube or with the electrolyte 62A, 62B, 62C or 62D in an electrolyte vessel. When the end of the capillary tube 30 dips into the electrolyte in an electrolyte vessel, an electrode manifold 301 energizes an electrode 52 in the electrolyte in the vessel. Thus, the desired electrolyte vessel is energized by the electrode 52 and selected by the capillary tube 30.

The electrolyte section 50 (FIG. 3) includes a motionless but easily removable electrode manifold 301 that dips multiple platinum electrodes simultaneously into all of the electrolyte vessels rather than dipping both the electrode and the capillary into the electrolyte vessels as described above to establish a potential across the tube. This action establishes one potential on the capillary tube 30 for electrophoresis with the other electrical connection to be described hereinafter as a permanent connection in a buffer although the circuit may be broken and established at programmed times.

Figure 2:
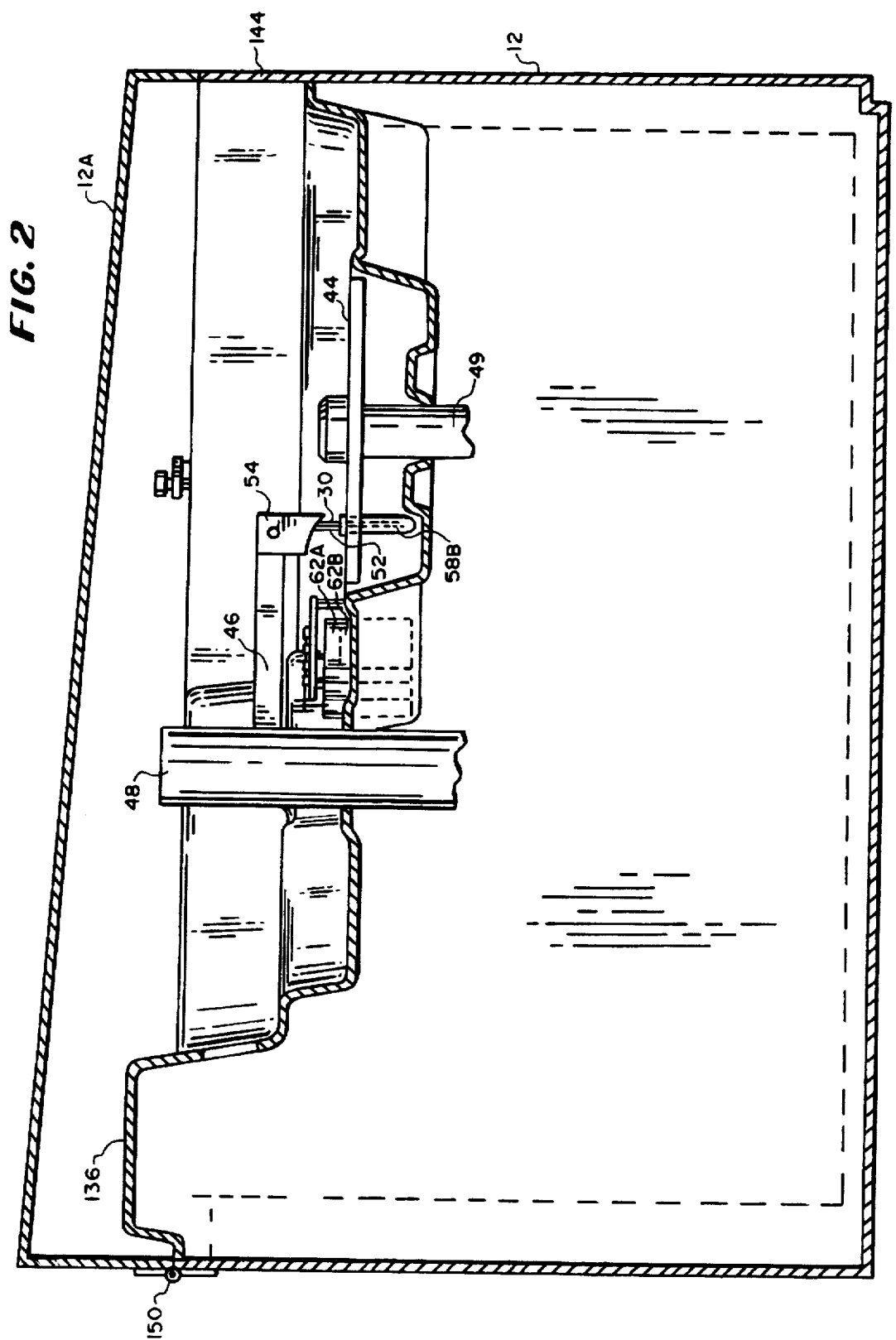
FIG. 2 is an irregular cross sectional view taken generally through a sample collecting mechanism of the apparatus shown in FIG. 1, looking from the left.

The electrode manifold 301 has four removable platinum wire electrodes 300A, 300B, 300C and 300D attached to it. These platinum wire electrodes 300A, 300B, 300C and 300D dip into four buffer electrolyte beakers 60A, 60B, 60C and 60D. Pivotally mounted grounding clapper 301A is released by an electromagnet (not shown in FIG. 1), located below the mounting surface 405 to act as a safety ground by swinging against the electrically conducting electrode manifold 301 when overhead access lid 144 in FIG. 2 is opened. Preferably, the grounding clapper 301A should incorporate a resistive path to ground and not a highly conductive path to ground so the high-energy sparks are not formed during the grounding process. High-energy sparks might disrupt nearby electronic circuitry.

The sensing section 18 (FIG. 1) includes an absorbance monitor 70 and a sensor 72 located inside sensor cassette 74. The absorbance monitor 70 and sensor 72 utilize the optics, circuitry and structure of the absorbance detector described in U.S. Pat. Nos. 4,726,680 and 4,523,097 for liquid chromatography absorbance detectors.

For capillary electrophoresis purposes, the detection volume, which limits the volume resolution of separated bands, is smaller than is usual for liquid chromatography absorbance detectors. The detection volume for capillary electrophoresis should be smaller than 100 nanoliters and often is in the range of 1 to 10 nanoliters. This is because of the very small volume of separated bands.

The absorbance monitor 70 incorporates a light source for illuminating one side of sensor 72 and a light detector for detecting light exiting the opposite side of sensor 72. It is substantially the same detector turned on its side so that the flow cell is on top and has a horizontal flow axis or plane, instead of being mounted on the side of the detector and having a vertical flow axis or plane. Of course, the flow cell and separating system are adapted for capillary electrophoresis as described herein, instead of for liquid chromatography as described in the foregoing patents.

To sense bands, the capillary tube 30 enters the sensor 72 through hole 38. Sensor 72 may be equipped with adjustable slits to align a very narrow measuring light beam so that it goes exactly through the liquid filled part of the capillary tube 30. The position of the slits is adjusted by screw adjustment 76 as described hereinafter.

To sense bands, the capillary tube 30 enters sensor 72 after passing through hole 38 in cassette 74. Sensor 72 may be equipped with fixed or adjustable slits to align a very narrow measuring light beam so that it goes exactly through the liquid filled part of the capillary tube 30. In some embodiments, the position of adjustable slits may be adjusted by screw adjustment 76 (FIG. 1) as described hereinafter but this is not necessary.

Figure 22:
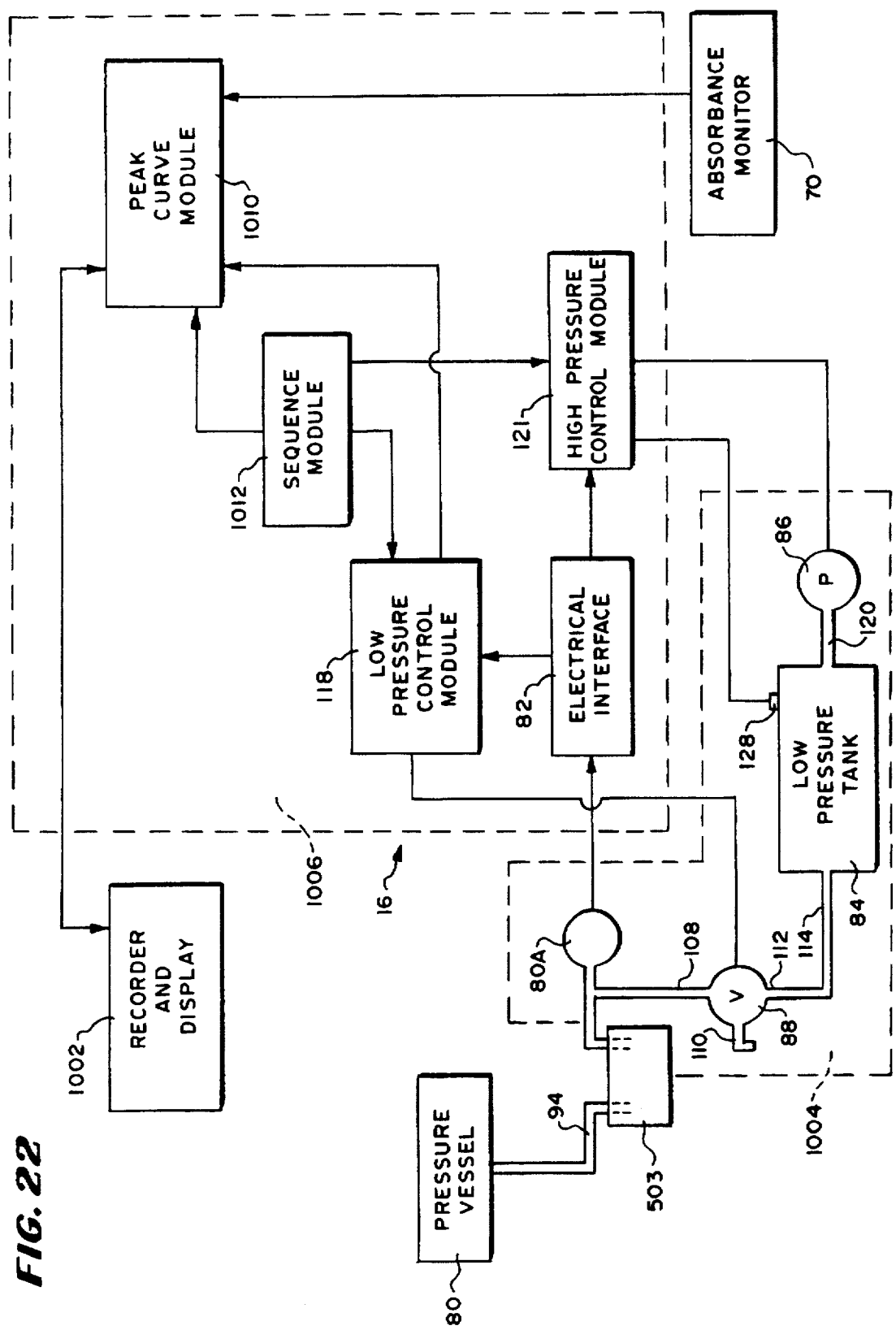
FIG. 22 is a block diagram of a system for controlling sample injection.

The sample injection system 16 (FIGS. 1 and 22) includes a controllable pressure buffer, the pressure vessel 80, an electrical interface 82, a low vacuum tank 84 and a pressure control solenoid valve 88. The pressure vessel 80 is connected by connecting tubing 94 to electrode and a liquid trap 503 (not shown in FIG. 1 but shown in FIG. 22) and communicates with the common port 108 of solenoid valve 88. It also communicates with the pressure sensor 80A through tube 94A to sense vacuum pressure in contact with the surface of the buffer during sample injection. Advantageously, tube 94A from the pressure sensor 80A may be directly connected to a pressure vessel 80 instead of being connected to tube 94 and liquid trap 503 (FIG. 22). Such connection (not shown) has the advantage of not producing pressure measurement error due to the velocity pressure drop in tube 94 and trap 503 (FIG. 22) when the valve 88 suddenly vents pressure vessel 80 to atmospheric pressure or if vessel 80 leaks. The pressure vessel 80 also may provide an electrical connection to the capillary tube 30 during electrophoresis.

The pressure sensor 80A is electrically connected through conductor 92 to the electrical interface 82, which in turn, supplies signals to the low pressure control module 117 and high pressure control module 119. The low pressure control module 117 controls the valve 88 and the high pressure control module 119 controls the pump 86. The electrical interface 82 may include an integrator to provide a signal proportional to the sample and may be performed in a computer connected to the electrical interface 82.

The capillary tube 30 extends into the fraction collector system 21 and is mounted to a movable lifting and rotating arm 460 of the carrier 411. The carrier 411 is partly filled with electrolyte buffer.

To establish an electrical connection through the capillary tube 30 for electrophoresis, the fraction collector system 21 receives electrode (not shown) in vessel 80 and the capillary tube 30 and this electrode dips into electrolyte buffer. The flexible conductor 90 is connected to this electrode and to the ground terminal 105 of power supply 14. Connecting tubing 94 pierces cap 98 but does not dip into the electrolyte buffer within the electrode buffer vessel 96.

To draw a controlled amount of sample into the end of the capillary tube 30 with a measured pressure: (1) connecting tube 94, the electrode and the capillary tube 30 are sealed air tight into the removable cap 98; (2) the removable cap 98 is sealed air tightly to vessel 80; and (3) the pressure sensor 80A communicates to the interior of an electrode buffer vessel 96 through tubes 94A and 94 and senses the pressure therein. The cable 92 connects the pressure sensor 80A to an electrical interface 82 which is connected by a lead 106 to a conventional controller or computer 119 not described in connection with FIG. 1. In the alternative, the signals may be recorded with conventional recording equipment and the operation of the sample injector and movable arm 46 may be manually performed.

To supply negative pressure to the vessel 80, the connecting tubing 94 communicates with the common port 108 of pressure control solenoid valve 88. Normally open port 110 of this valve is vented to the atmosphere and the normally closed connection 112 of this valve is connected to tubing 114 which leads to low-vacuum tank 84 so that energization of the pressure control solenoid valve 88 applies vacuum pressure to the vessel 80.

To energize the pressure control solenoid valve 88, a conductor 116 is electrically connected to a controller or computer 119 or to a manually-operated electrical switch 117 connected to a source of power and supplies power to the solenoid of the pressure control solenoid valve 88. This controller or manually-operated electrical switch supplies signals to initiate the sample injection while the capillary is held in the sample well by the movable arm 46.

To maintain the vacuum pressure in the low-pressure vacuum tank 84, tubing 120 connects the low-pressure vacuum tank 84 to vacuum pump assembly 86. The vacuum pump assembly 86 includes a vacuum pump 122 mechanically connected to electric motor 124 through coupling 126. A vacuum sensor 128 turns motor 124 on or off by comparison with a standard in computer module 119 which connects vacuum sensor 128 and motor 124 when the pressure in the tank 84 becomes too low or too high. This establishes a controlled negative pressure in the tank 84. Preferably, the setting of the vacuum sensor 128 is adjustable or programmable through the computer module 119.

The high voltage power supply 14 is located inside the cabinet 12 and is fitted with ground terminal 105 and high voltage terminal 132. The power supply 14 is preferably capable of supplying a regulated voltage from 1,000 to 40,000 volts at a current of up to 400 microamperes. A high voltage insulated cable 134 is connected to high voltage terminal 132 and terminates (connection not shown) in platinum wire electrode 52 and electrode manifold 301.

A conventional air cooling and temperature control unit (not shown) are housed in cabinet 12. A fan incorporated in this unit blows temperature conditioned air out through vent slots 140 located in venting unit 136 (FIG. 2). Return air to the air conditioning mechanism is through vent slots 138. This air conditioning feature ensures that the electrophoresis process operates at a repeatable temperature that does not vary significantly over a period of time. The air enters and flows above the sensor 72, blows through heat transfer fins 76A, which are thermally connected to sensor cassette 74, thence to capillary tube 30 and sensor 72, and then is routed past the capillary tube 30 between its sample inlet end and the sensor 72 by conventional baffling not shown in this figure. Temperature control of electrophoretic separations is a common feature of electrophoresis apparatus. In the context of accurate sample injection, it is important that the liquid contents of the capillary tube 30 remain at a repeatable temperature and therefore at a repeatable viscosity.

The air supply vent slots 140 are thermally coupled to the sensor 72 under sensor mounting plate 302 in FIG. 1 herein. The sensor 72 is temperature controlled by the air exiting the vent slots 140 as it passes through fins 76A mounted on sensor cassette 74. The sensor cassette 74 and the sensor 72 located directly beneath it are removably fastened to the absorbance detector by captivated by loosenable mounting screws (not shown).

In FIG. 2, there is shown a sectional view of the cabinet 12 taken through lines 2—2 of FIG. 1 and showing the rotor head 48, movable arm 46, capillary tube 30, sample vials such as 58B and a lid 144. As shown in this view, the cabinet 12 is: (1) insulated; (2) includes a top surface 12A that slopes upward from front to back; and (3) is fitted with a lid 144 which preferentially has metal sides and a transparent top. The lid 144 is hinged to the cabinet 12 with hinge or hinges 150. The cabinet 12 preferentially has an outer metal surface which, along with the sides of the lid 144, are electrically grounded for safety. As shown in this view, the bracket 54 mounts the capillary tube 30 at a location adjacent to the electrode 52 so that the capillary tube 30 is insertable into the sample vial 58B and the electrode 52 may be moved to the buffer vessel 62A for insertion in the buffer 60A (FIG. 1) by rotating the movable arm 46.

When a new sample is desired, a rotor 49 rotates a sample housing reel 44 to move a new sample in position under the arm 46 and the arm 46 is swingable between the buffer vessel 62A and the sample housing reel 44. As it rotates, the capillary tube 30 extends through the notch 40 (FIG. 3) in the removable horizontal ledge 34 (FIG. 3) where it is inserted into coils therein which expand or contract to take more or less tubing as the arm 46 moves. With this arrangement, the capillary tube 30 remains horizontal between its connection with the bracket 54, the recess in the horizontal ledge 34 (FIG. 3) and the sensor 72 (FIG. 1).

In FIG. 3, there is shown a simplified fragmentary view of a movable arm 46, a flexible electrical conductor 134 for high voltage, a capillary tube 30, and a sensor 72 with the capillary tube 30 being positioned in a recess in the ledge 34 (the cover plate 32 is removed in this view). The bracket 54 is shown having an opening adapted to mount one end of the capillary tube 30 for movement from sample to buffer. As best shown in this view, the horizontal ledge 34 includes a recess in which the capillary tube 30 is coiled so that it may receive more or less tubing as the movable arm 46 swings between a buffer location and a sample location. The bracket 54 supporting the capillary tube 30, the recess in the ledge 34 and the fitting for the sensor 72 are all in the same horizontal plane so that, as the electrophoresis apparatus is operated, the capillary remains horizontal.

Typically, the inside diameter of the tube 30 is 50 to 75 micrometers and the outside diameter is 375 micrometers. The length of the interior of the tube is filled with a liquid buffer electrolyte. An electric field is established along the axis of the tube 30 by conventional means and electric current flows through the tube.

Figure 4:
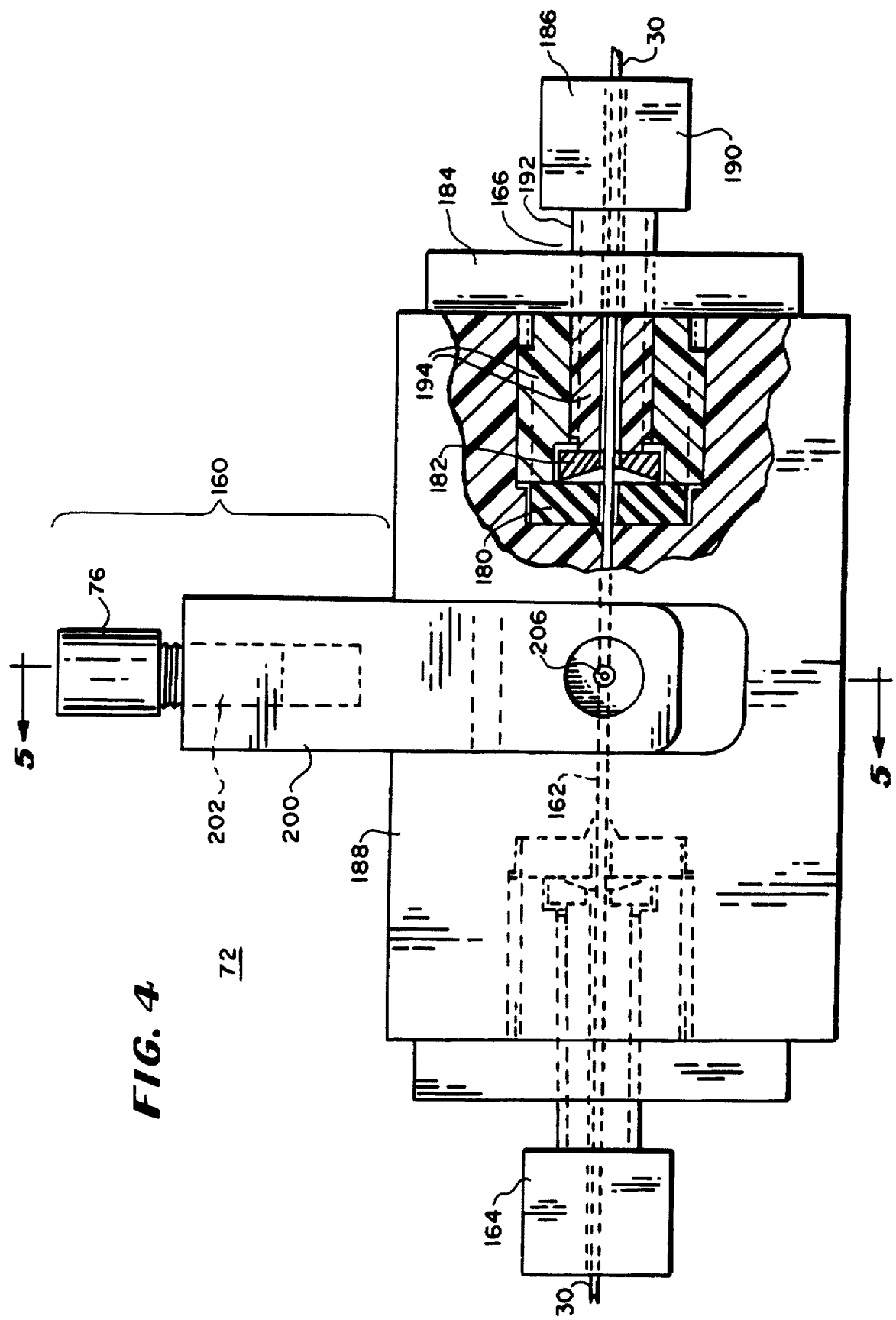
FIG. 4 is a side elevational view, partly broken away and sectioned, of a flow cell useful in an embodiment of the invention.

In FIG. 4, there is shown a side view partly broken away and sectioned showing the sensor 72 having an adjustment section 160, an optical slit section 162, a first fitting assembly 164 for the capillary tube 30, and a second fitting assembly 166 for the capillary tube 30. The capillary tube 30 is received in the first and second fittings 164 and 166, which cause the capillary tube 30 to extend along the axis of the sensor 72 and between the slits in the optical slit section 162. The location of the two slits in a direction perpendicular to the axis of the capillary tube 30 is adjusted by the adjustment section 160.

The sensor 72 is attached to a cassette or mounting plate for mounting in the absorbance monitor 70 (FIG. 1) and receives the capillary tube 30. To mount the capillary tube 30, the two fitting assemblies 164 and 166 are adjustable. They are identical in structure and only the second fitting assembly 166 will be described in detail herein.

The second fitting assembly 166 includes a rubber washer 180, a stainless steel squeezer 182, a plastic threaded closure 184 and a plastic threaded fastener 186. The threaded fastener 186 is positioned to be tightened to hold the threaded closure 184 in place where it supports a threaded sleeve. The threaded fastener 186 also presses the stainless steel squeezer 182 against the rubber washer 180 to provide a seal around the capillary tube 30.

In this embodiment, a housing 188 of the sensor 72, the threaded fastener 186 and the threaded closure 184 are all formed of a relatively hard plastic such as Delrin (trademark of the DuPont Corporation). The rubber washer 180 is a flexible, elastomeric material which may be the thermoplastic rubber Kraton. A central aperture extends through the rubber washer 180, the stainless steel squeezer 182, the threaded closure 184 and the threaded fastener 186 to accommodate the capillary tube 30 which extends along the longitudinal axis, past the optical slit section 162 where the optical sensing is performed and through the first fitting assembly 164 on the opposite side of the sensor 72.

To force the rubber washer 180 around the capillary tube 30, the rubber washer 180 is generally cylindrical with a cylindrical central opening receiving the capillary tube 30. It fits conformably in a counterbore within the housing 188 of the sensor 72. The stainless steel squeezer 182 is generally cylindrical but has an inwardly tapering cone positioned adjacent to the rubber washer 180 and a central aperture to accommodate the capillary tube 30 so that when it is pressed inwardly, it forces the rubber washer 180 inwardly towards its central opening and outwardly against the counterbore.

To force the stainless steel squeezer 182 against the rubber washer 180, the threaded fastener 186 includes a thumb handle 190 and a threaded shank 192, with the threaded shank 192 extending downwardly through the plastic threaded closure 184 where it engages a correspondingly threaded metal sleeve 194 threaded into a tapped hole of the Delrin housing 188. The threads within the tapped hole are within a metal sleeve molded within the aperture of the Delrin housing so as to remain fixed in position and still accommodate threads. The mechanism of the fittings are designed to accommodate the capillary tube 30 in such a way that the capillary tube 30 is held immobile in the light sensor 72.

The adjustment section 160 includes an adjustment screw 76 fixedly mounted (by conventional means not shown in the figure) with respect to the housing 188 and an optical slit carriage 200. The optical slit carriage 200 is stainless steel and threaded at 202 in its upper portion with internal threads complementary to the external threads on a shank of the adjustment screw 76 so that as the adjustment screw 76 is rotated, the carriage 200 is moved up and down with respect to the housing 188 of the sensor 72.

Figure 5:
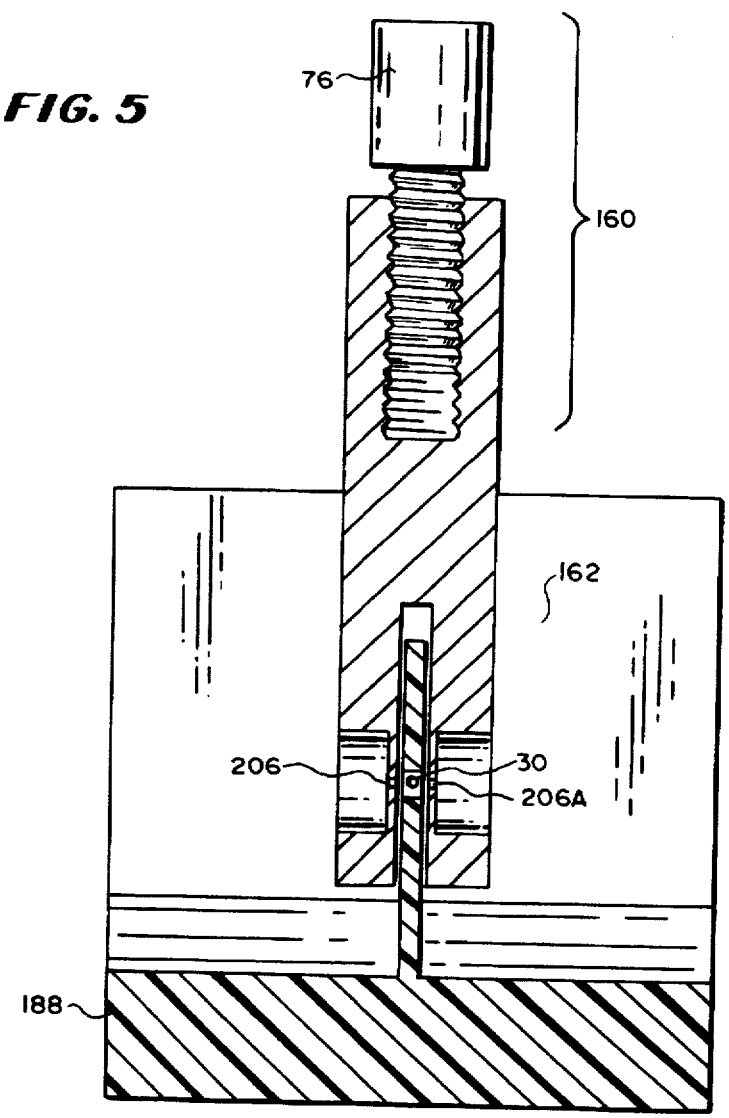
FIG. 5 is a sectional view taken through lines 5—5 of FIG. 4.

The optical slit section 162 is mounted to the bottom of the optical slit carriage 200 to be raised and lowered therewith and includes on each side a relatively short optical slit 206 having a longitudinal axis aligned with the longitudinal axis of the capillary tube 30. There are two such slits which closely straddle the capillary tube 30 (FIG. 1). This is not clearly shown in FIG. 5 which is a cross section through line 5—5 of FIG. 4. FIG. 5 more clearly shows the relationship of the two slits 206 and 206A to the capillary tube 30 and the narrow dimension of the slits, which are 100 micrometers in the preferred embodiment. Preferably, the distance between the slits is between one and three times the outside diameter of the capillary tube 30.

More specifically, the rubber washer 180 is compressed around the capillary tube 30 to hold the tube in place. The rubber washer 180 preferably is made of white, food grade, Kraton (trademark) thermoplastic rubber which does not deposit any ultraviolet light absorbing materials on the quartz tube as the tube is pushed through the washer. Kraton is available from Shell Corporation. The rubber is compressed radially to tighten around the tube by pushing the female cone-shaped stainless steel squeezer 182 against it by turning a plastic threaded fastener 186. The threaded fastener 186, stainless steel squeezer 182 and rubber washer 180 are captivated within the housing 188 of the light sensor 72 by the threaded closure 184 which screws into a threaded recess in the housing 188. The tightener, captivator and housing are advantageously made out of Delrin (trademark of DuPont) plastic.

Figure 6:
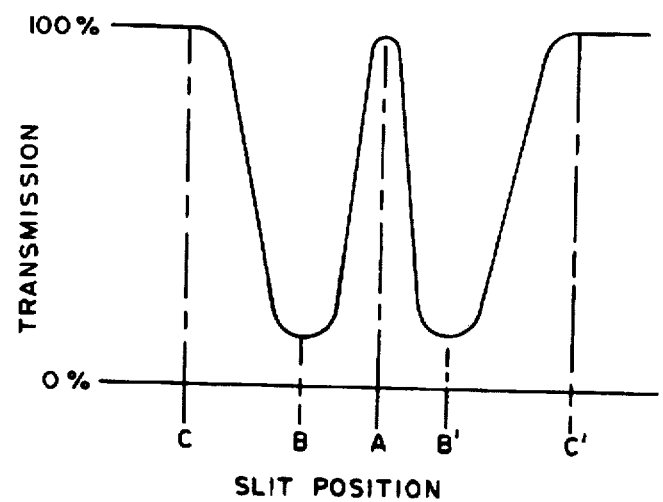
FIG. 6 is a graph of a curve representing transmission with different positions of slits in the embodiments of FIGS. 4 and 5.

In one embodiment, the optical slit carriage 200 is moved with the adjustment screw 76 to center a pair of optical slits, one of which is shown at 206, each being 0.01 inch (250 micrometers) long by 0.004 inch (100 micrometers) wide, over the capillary tube 30 extending through the light sensor 72. However, the slits may be fixed in position. The dual slits are exactly corresponding elements mounted exactly opposite each other across a bifurcation of the optical slit carriage (FIG. 6). The capillary tube 30 lies within the bifurcation. The long direction of the slit is parallel to the axis of the capillary tube 30. When the adjustment screw 76 is turned in the adjustable slit embodiment, the optical slit 206 moves transversely with respect to the capillary tube 30. The capillary tube 30 is firmly held within the bifurcation by two holders.

The sensor system 18 (FIG. 1) is inserted in the absorbance monitor 70 (FIG. 1) located within the cabinet 12 in FIG. 1. In FIG. 1, the sensor is generally shown at 18. The capillary tube 30 is filled with water or buffer. Light from the light source of the absorbance monitor 70 (FIG. 1) enters one of the pair of slits in the sensor system 18 (FIG. 1), and when the sensor system 18 (FIG. 1) is properly adjusted, light exits the other slit and impinges upon the light detector of the absorbance monitor 70 (FIG. 1). To make this adjustment, the adjustment screw (shown as 76 in FIG. 4) is rotated and the indication of the absorbance monitor 70 (FIG. 1) is monitored. Starting at one extreme of rotation on the adjustment screw 76, and referring to FIG. 6, the following is observed.

At slit position C, the slit is entirely beyond the capillary tube 30 and light travels through the free space between the pair of slits. As the adjustment screw 76 is rotated, the light beam cuts through the curved edge of the capillary tube 30 which deflects most of the light going through the first slit so it does not go through the second slit. At slit position B, almost all of the light is lost, and a minimum of light transmission is indicated on the absorbance monitor 70 (FIG. 1).

Assuming that the capillary tube 30 is properly filled with water or electrolyte buffer (no air in the tube at the light path), continued rotation of the adjustment screw 76 until the pair of slits are centered on the tube greatly increases the transmission again. There is a well defined maximum at proper alignment. This is shown as slit position A in FIG. 6.

Further rotation of the adjustment screw 76 produces transmission indications as shown when moving from A (FIG. 1) to B' (FIG. 1) and then from B' (FIG. 1) to C' (FIG. 1) because of symmetry in the transverse direction. The absorbance monitor 70 (FIG. 1) should be operated with the adjustment screw 76 set to slit position A (FIG. 1), as determined from the local maximum transmission reading of the absorbance monitor 70 (FIG. 1) itself.

Although the foregoing describes a flow cell with adjustible slits, there is no intention to argue that this arrangement is necessarily superior to a flow cell having a fixed aperture. The description is included only to provide information about one of a number of flow cell arrangements suitable for capillary electrophoresis.

In FIG. 7, there is shown a fragmentary elevational view, partly sectioned and broken away, of the lifting and rotating arm 460, the carrier 411, and a sample collection cup 430. The lifting and rotating arm 460 has one end of the capillary tube 30 mounted through it for carrying upwardly and downwardly to move it into position for electrophoresis and sample collection and into another position for participation in the sample injection procedure.

The sample cups, such as the sample collection cup 430 are adapted to be moved by the carrier 411, one at a time into a location where the capillary tube 30 will be inserted into the buffer in the cup well 430A which communicates through semipermeable membrane 430B to the buffer 451 in the carrier 411 to permit electrophoresis of samples into individual cells such as cup 430 for concentration in a manner to be described hereinafter against a membrane located near their bottom within the buffer 451 in cell well 430A.

The sample cups are similar in construction to the sample cup 80 in FIG. 13 of U.S. Pat. No. 4,164,464, the disclosure of which is incorporated herein by reference. The fraction collector system 21 (FIG. 1) includes a rack 802 by which a plate 410 and carrier 411 may be moved and first and second electrical switches 201A and 201B which may be used to electrically connect either side of a dividing wall 452 of the carrier 411 to either ground or to disconnect the sides. Instead of a ground connection through conductor 90A or 90B, a low voltage (with respect to ground) supply 135 may be used.

With this arrangement, migration in either direction may be accommodated within the cells and the carrier 411 may be removed from its interlocking position in the plate 410 for sample concentrating or may remain within the capillary electrophoresis apparatus 10 during concentration of the sample within the cells. The direction of migration is controlled by selecting the proper potential to move the more dilute molecular species across a bridge 453 to the other compartment for concentrating against the membrane at the bottom of the compartment. To concentrate the sample, the buffer liquids are generally raised above the bridge 453 a slight amount.

To align and move the carrier 411, sample cup by sample cup, during use, a rack 802 extends below support blocks 405 and 409 and between them for engagement with a pinion (not shown in FIG. 7). This permits the movement of the support blocks 405 and 409, the support plate 410, the carrier 411 and the vessel (not shown in FIG. 7) mounted within the support plate 410 along parallel guide rails 406 and 407 which are engaged by the support blocks 405 and 409. The support blocks 405 and 409 are fastened to the support plate 410 which removably engages the carrier 411 (not shown).

Figure 20:
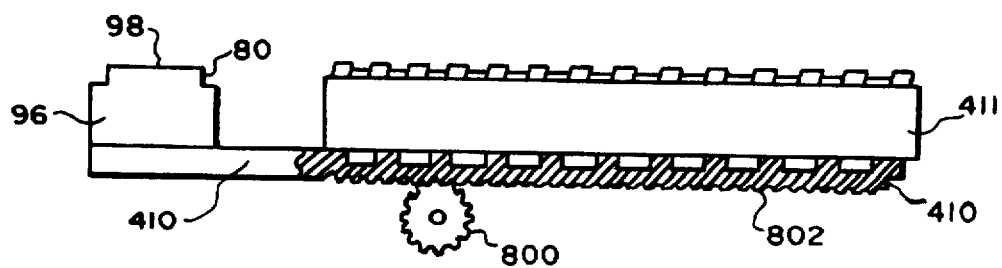
FIG. 20 is a side elevational view of a fraction collector used in an embodiment of the invention in forming a part of FIG. 1.

The vessel 80 (FIG. 1) is mounted in a recess in the housing 12 (FIG. 1) to the support plate 410 and moves with the carrier 411 (FIG. 20). To connect the capillary tube 30 to the cap 98 (FIG. 1) and the vessel 80 (FIG. 1), the latter are slid into position under the capillary tube 30. Capillary tube 30 is sealably guided into cap 98 (FIG. 1) by threaded, tightenable bushing 400, cap sealing pierce 400A, and tube fixing elastic washer 400B. Bushing 400 is screwed into lifting and rotating arm 460. Screwing in bushing 400 compresses washer 400B against sealing piece 400A, forcing the washer 400B to hold capillary tube 30. The lifing and rotating arm 460 is supported by lifting and rotating rod 470. Lifting and rotating rod 470 is lifted and rotated by lifting and rotating mechanism 404, shown in phantom.

To collect fractions, the sample cup 430 has two cells containing electrolyte, indicated as 430A and 430B. The bottoms of the wells are covered with clamped-on semipermeable membrane assemblies 430D and 430C respectively to permit the flow of buffer ions but not the migration of separated sample. Electrical continuity for the electrophoretic migration taking place in capillary tube 30 is provided through the electrolyte in cell well 430A, the assembled semipermeable membrane 430D, electrolyte buffer 451 residing the carrier 411, an electrode 505 and the conductor 90 leading to electrical ground.

Separated zones are electrophoretically eluted or electrosmotically discharged from the capillary tube 30 into the electrolyte in cell well 430A, where they are trapped by the semipermeable membrane assembly 430D. Each sample cup, such as 430, has a connecting bridge 453 which provides fluid and electric connection between wells 430A and 430B if the electrolyte level is higher than that shown in FIG. 7. The bridge 453 is supported by supporting wall 452 which is a part of carrier 411.

To keep the separated samples in cell well 430A and prevent them from being transported to well 430B, either: (1) the level of the electrolyte or buffer in the wells 430A and 430B is lower than the height of the top of the bridge 453; or (2) the electrolyte or buffer level 450 and 451 in the two sides of the carrier 411 are lower than the height of the top of the supporting wall 452. Because of the possiblity of capillary forces drawing electrolyte within the carrier 411 over the space between the supporting wall 452 and the bridge 453, the electrolytes in the wells 430A and 430B preferably are lower than the height of the bridge 453 during this type of fraction collection.

The carrier 411 is supported by support plate 410, which in turn is supported by bearing blocks 408 and 409 which ride on guide rails 406 and 407. This permits the carrier 411 to slide in the direction perpendicular to the plane of FIG. 7 after the capillary tube 30 is withdrawn from the sample cup. The lifting and rotating mechanism 404 lifts arm 460 to effect this withdrawal. The position of the capillary tube 30, arm 46, bushing 400 and lifting and rotating rod 470 are shown in phantom (FIG. 7) as 30A, 460A, 400A and 470A respectively. In the phantom position the capillary tube 30 is lifted above the top of carrier 411 and a conventional indexing mechanism (not shown in FIG. 7) moves the support plate 410, bringing the next sample collection cup into position for fraction collection, or the conical hole 501 (FIG. 13) in the removable cap 98 (FIG. 1) into position under the capillary tube 30 for injection of the next sample.

Figure 8:
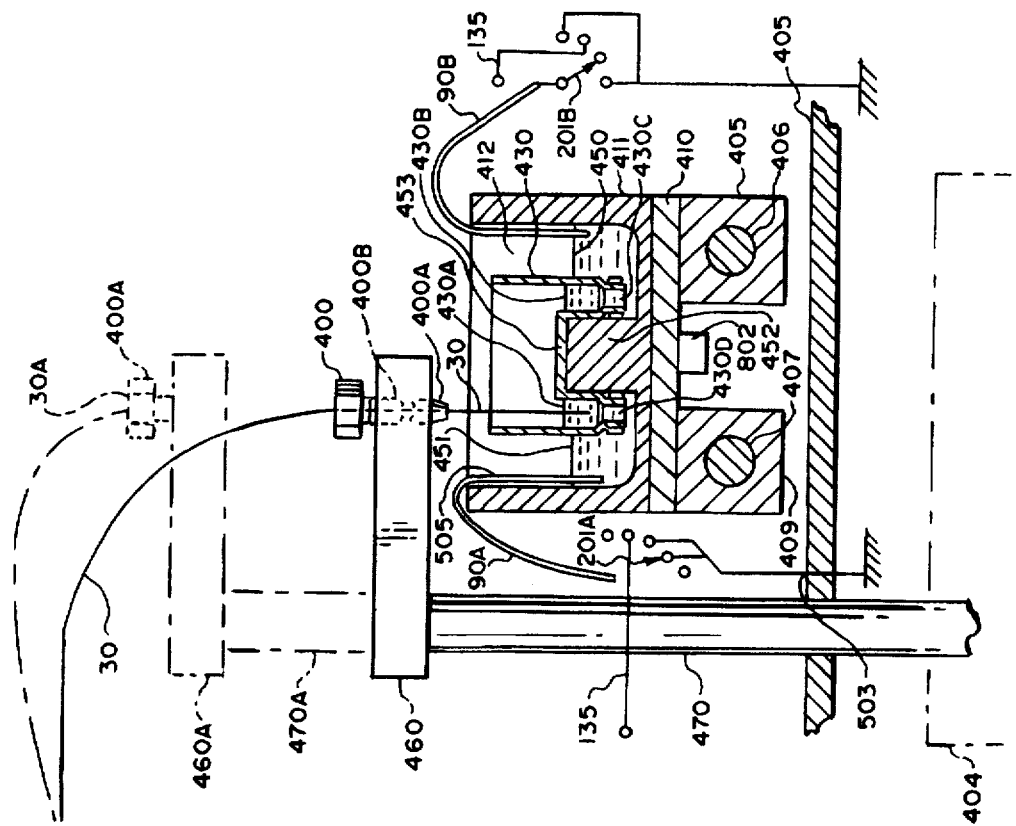
FIG. 8 is a cross section taken through the same plane as FIG. 7, showing another part of the operating cycle of the fraction collector.

In FIG. 8, there are shown two further positions of the capillary tube 30, the arm 460 and lifting and rotating rod 470 of the lifting and rotating mechanism 404. The two positions are the collecting position (drawn solidly) and 30B at the waste position (drawn in phantom), corresponding to the two different rotational positions of arm 460 and lifting and rotating rod 470.

To move from the collecting position to the waste position 30B in FIG. 8, the arm 460 first is lifted by the rotating and lifting mechanism 404 to the position shown in phantom in FIG. 7. The waste (phantom) position of the capillary tube (30B) in FIG. 8 is used when no material of preparative interest is coming out of the capillary tube. Such waste material is discharged into the buffer 451 residing in carrier 411; and may be discarded later. The phantom position in FIG. 8 also corresponds to the sample injection postion for the arm 460 and capillary tube 30 shown in FIG. 1. The arm 460 can also rotate to place the capillary tube 30 in electrolyte residing in well 430B in the other side of the cups 430 (FIG. 7).

Figure 9:
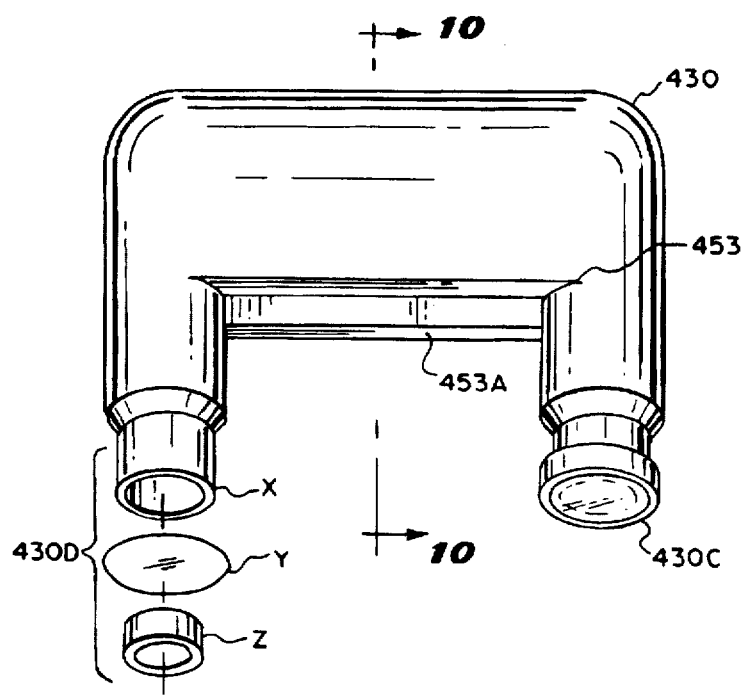
FIG. 9 is a perspective view of a sample collecting and concentrating cup, incorporating a trap, used in the fraction collector of FIGS. 1, 7 and 8.

In FIG. 9, there is shown an exploded perspective view of one sample collecting cup 430. The exploded view shown at 430D indicates how a semipermeable membrane may be assembled to the sample cup. As shown in this view, the sample cup includes a tubular cylinder X extending downwardly and forming walls of the well, a semipermeable membrane Y of diameter somewhat larger than that of the outside diameter of cylinder X, closing the well and an elastic band or ring Z of inside diameter somewhat smaller than the outside diameter of cylinder X. The semipermeable membrane Y is laid over the tubular cylinder X and the elastic band Z is forced over to seal it in place. The complete assembly is shown at 430C.

Figure 10:
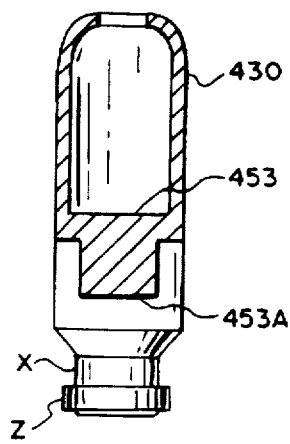
FIG. 10 is a cross section taken through 10—10 of FIG. 9.

The sample cup 430 has a key 453A molded into it, under the lower surface of bridge 453. This may be seen more clearly in FIG. 10 which is a sectional view taken through plane 10—10 in FIG. 9. Key 453A fits into one of the several slots 601A, 602A, 603A etc. in dividing wall 452 as shown in FIGS. 11 and 12.

Figure 11:
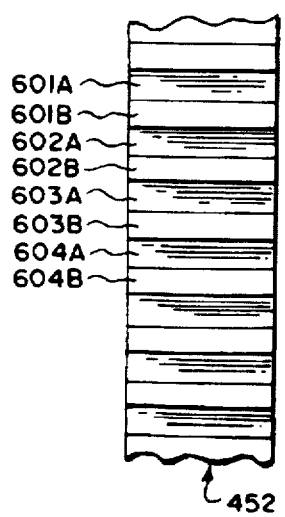
FIG. 11 is a top view of a supporting wall forming a part of the fraction collector of FIGS. 1 and 7–10.
Figure 12:
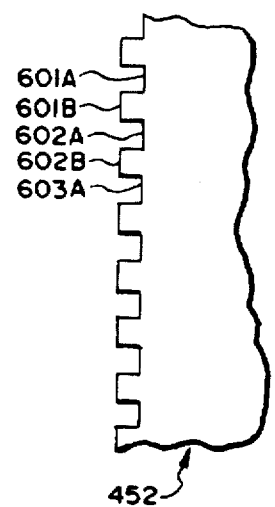
FIG. 12 is a side view of the supporting wall of FIG. 11.

FIG. 11 is a top view of the dividing wall 452 of carrier 411 (FIG. 7). FIG. 12 is a broken-out section of the side view of the same wall 452. The key 453A (FIG. 9) and aforementioned slots are sized and spaced such that sample cups 412 through 448 (FIG. 1) are located close together and accurately positioned within carrier 411 (FIGS. 1 and 7). This is necessary so that the indexing mechanism (not shown in FIG. 9) that moves carrier 411 along guide rods 406 and 407 (FIG. 7) can accurately position the sample cups under the capillary tube 30. Alternatively, the sample cups may be fastened together rather than loose from each other, and only one locating or keying feature used for each group of fastened-together sample cups.

For fraction collection, operation starts in an initial cup 412 and proceeds in any one of several fraction collection patterns known in the art until collection is complete. FIGS. 13 and 14 may be used to explain a particular fraction collection cycle for one collecting tube. Reference is also again made to FIGS. 7 and 8.

Assume observation starts just before sample is to be collected in cup 430. Initially the arm 460 is positioned as shown at 460A in FIG. 7 with the capillary tube 30 above the well 430A in sample cup 430. The high voltage has already been turned off by a conventional programmer which is not shown. Lifting and turning mechanism 404 lowers the arm into the position indicated as 460 in FIG. 7. This lowers the capillary tube 30 into the electrolyte in well 430A of sample cup 430. This is called the "collection" position. After the capillary tube 30 has been lowered into the electrolyte in well 430A and electrical continuity has been established, the programmer turns the high voltage power supply on and electrophoresed and or electro-osmosed material leaves the capillary tube 30 into the electrolyte in the collecting well 430A. This material from the capillary tube 30 contains the sample component of interest. Solute in this material is trapped in the well, as it cannot pass through the semipermeable membrane at the bottom of the well.

When the sample component of interest has been completely eluted into the well, the programmer turns the power supply off. Then the lifting and rotating mechanism 404 raises the arm 460 to the position shown as 460A in FIG. 7. Next, the lifting and rotating mechanism 404 rotates the support rod 470, rotating the arm 460 to the position shown in FIG. 14. The lifting and rotating mechanism 404 then lowers the arm 460, putting it into the position shown in phantom in FIG. 8, with the capillary tube 30 being in position 30B where it dips into the electrolyte 451 within the carrier 411. This is called the "waste" position, and electrical continuity is re-established there. The programmer then turns the high voltage on and waste material between collected sample zones is eluted into the electrolyte 451 which later may be discarded.

When the next zone or peak of desired sample to be collected is about to be eluted, the programmer turns the power supply off and then lifts arm 460, the indexing mechanism (not shown in FIG. 7) advances the carrier 411 by rotating a pinion against a rack 802 one sample cup width towards the top of FIG. 14, the arm 460 is rotated so that it is in the position perpendicular to the carrier 411 such as in FIG. 13 and the arm 460 holding the capillary tube is re-lowered, this time into the next sample collecting cup 431. Then the programmer turns the high voltage on again.

This pattern repeats continuously. It is not limited to continuously going from one sample cup to the next higher numbered, cup however. For example, with preparative work it may be desirable to make ten repeated, identical separations from a first sample located in sample changing system 20 (FIG. 1) and collect say, three sample components or fractions from each separation; and then go back to the same sample and do the same.

In a case like this, where there are three sample fractions to be collected from one sample in ten completely identical separation processes, it is advantageous to collect the first separation in the first, second and third cups, then back up the carrier and sample cups to the first cup again, and collect the second of the ten identical separations in the same three cups and repeat this process for ten times thereby saving on the use of cups and improving the yield due to less cup surface area that the sample might adsorb upon. Next, the three components of the second sample located in sample changing system 20 would be collected ten times in the fourth through sixth cups, and so forth.

An important advantage of using sample cups such as cup 430 is that they can be used for concentrating the separated sample component after the elctrophoretic separation. This is done in a way similar to that described in U.S. Pat. No. 4,164,464. Generally, the sample cups such as 430 are stacked side-by-side in a carrier 411 which has been removed from the electrophoresis apparatus and then the samples are concentrated in the carrier 411 by applying a potential across the buffer as explained more fulling in the aforementioned United States patents and the description hereinafter.

Figure 15:
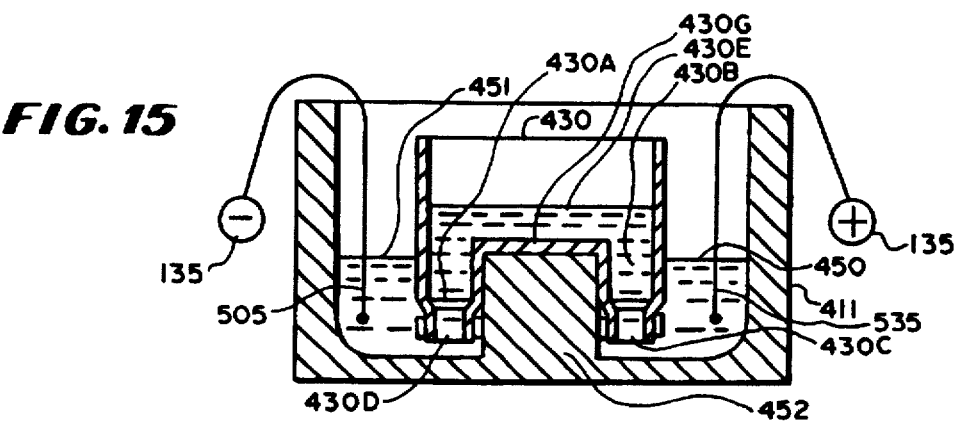
FIG. 15 is a fragmentary schematic sectional view of a sample collecting and concentrating cup and fraction collector as used for the reconcentration of samples in a membrane trap after their dilution during the initial fraction collection process.

In FIG. 15, there is shown a cross sectional view of a cup 430 in a carrier 411 having more electrolyte buffer added to the cup so that the electrolyte covers bridge 453 as shown at 430E. Electrodes 505 and 535 are laid in electrolyte solutions 451 and 450 within carrier 411 and extend almost the full length within carrier 411. Electrolytic solutions 451 and 450 are mechanically and electrically separated by dividing wall 452. A potential difference of 100 to 200 volts is apppplied to electrodes 505 and 535 and differentiated by the symbols "−" and "+" at 135. Positively charged sample molecules in well 430A then migrate downwards and are trapped above the top surface of the semipermeable membrane shown at 430D.

After sufficient time has elapsed for concentration to take place, the sample cups are removed and placed vertically with the semipermeable membranes laying upon a firm surface. The concentrated sample lying just above the membrane may be pipetted off for further use at this time. In case the sample adheres to the membrane, the voltage on the electrodes 505 and 535 may be momentarily reversed to migrate the sample off the membrane or the membrane may be removed as indicated in FIG. 9.

Alternatively, concentration may be effected by using switch 201A–201B which is shown in FIGS. 7 and 8. It may be used to introduce the 100 to 200 volt potential difference electrolyte solutions 451 and 450. This allows concentration without removal of carrier 411 from the electrophoresis apparatus in FIG. 1. It also allows filling the cup 430 with buffer above the level of bridge 453 (FIG. 7) before electrophoresis takes place.

The polarity of the electrode voltages in FIG. 14 is that which would be selected for positively charged sample molecules. If the sample is negatively charged, the polarity of the electrodes 505 and 535 may be reversed from that shown in FIG. 15. Alternatively, the electrode potentials may be kept the way they are shown in the figure and the sample cup turned around so that the sample collecting well 430A is in contact with the electrolyte solution 450 adjacent to the positive electrode if concentrating time is not a factor. Thus, the positioned orientations shown in FIG. 15 may be maintained, and negatively charged sample being concentrated from well 430A will move across the bridge 453 through the bridge electrolyte 430E and be concentrated in well 430B which now will be reversed to the position 430A on FIG. 15.

If the sample component being collected is composed of relatively large molecules, of molecular weight over about 3000 daltons, the semipermeable membrane may be of fine-pored, relatively uncharged membrane such as fine-pored cellophane. Proteins are an example of such large molecules which will be trapped by fine-pored cellophane. If the sample components being collected are composed of molecules so small they can pass through the finest-pored cellophane, a specific ion-transmitting membrane can be used instead at 430D and 430C (FIG. 7) to trap the sample components. An example is Nafion (trademark of E. I. DuPont de Nemours) which preferentially passes only cations (positively charged ions).

In this example, buffer electrolyte cations in electrolyte solutions 451 and 450 in the carrier 411 can pass through the specific ion membranes. During fraction collection, since membrane preferentially passes only cations, anionic (negatively charged) analate species will not pass through the membrane and will be trapped in the well 430A. For post-collection concentration (FIG. 15), the polarities of the potentials applied to electrodes 505 and 535 are reversed from that shown in this figure.

Buffer cations in negative potential electrolyte solution 451 pass through the membrane at 430D, up well 430A, above bridge 430G, down well 430B, through the membrane at 430C and into positive potential electrolyte 450. Buffer anions cannot pass through either membrane. The flux of buffer cations within the cup 430 sets up an electric field that attracts the anionic analate within the cup towards the specific ion membrane at 430D. Analate molecules cannot pass through this specific ion membrane since they have the wrong charge to do so, and will concentrate above the membrane.

If the separated sample molecules (analate species) are cationic (positively charged), the membranes used at 430C and 430D may be anion-passing specific ion membranes. These will pass buffer anions to maintain electrical continuity during fraction collection and concentration, but trap the cationic analate. Of course, both the electrophoresing high voltage and the concentrating low voltage are reversed for separating cationic instead of anionic analate. The electrode polarities shown in FIG. 15 are proper for concentrating cationic analate. The high voltage electrophoresis voltage applied to vessels 60A, 60B, 60C or 60D (FIG. 1) should be negative for anionic analate and positive for anionic analate if electroosmotic flow in the capillary is not an oppositely-dominating factor.

Some sample materials of interest, such as DNA, have a tendency to adhere to cellophane membranes. A known apparatus for electro-concentrating DNA without it contacting a membrane is the so-called "salt trap".

A salt trap contains a region of high concentration (ca 7 molar) of a salt such as ammonium acetate. This salty region has a first end in electrical contact to a first polarity of a source of potential. A much less concentrated buffer solution containing the material or sample to be concentrated overlaid above the second end of the salty region. The highly concentrated salt solution is more dense than the less concentrated buffer solution, so the latter floats stably above the denser soluton below it. This upper solution is in electrical contact with a second polarity of potential. The usual arrangement of a salt trap is to have the dense solution located in the bottom of a "U" tube. One arm of the "U" tube is under the dilute buffer containing the sample to be concentrated. The second electrical contact is made to the dilute buffer. The other arm of the "U" tube is submerged in a surrounding tank of low density buffer which makes the first electrical contact.

When a voltage of proper polarity is applied between suitably arranged electrodes, charged sample migrates into the top of the concentrated solution in the side of the "U" tube under the sample-containing buffer. To maintain local conservation of charge, ions of the dense salt solution migrate out the other end of the "U" tube. Since the salt solution in the "U" tube is concentrated, a large amount of sample will migrate into the trap before any of it starts to migrate out the other end. However, this U-tube arrangement is inconvenient because it requires careful technique to remove the dense solution and sample from the "U" tube without disturbing hydrostatic equilibrium with respect to the overlying buffers, and thereby losing some of the sample.

Figure 16:
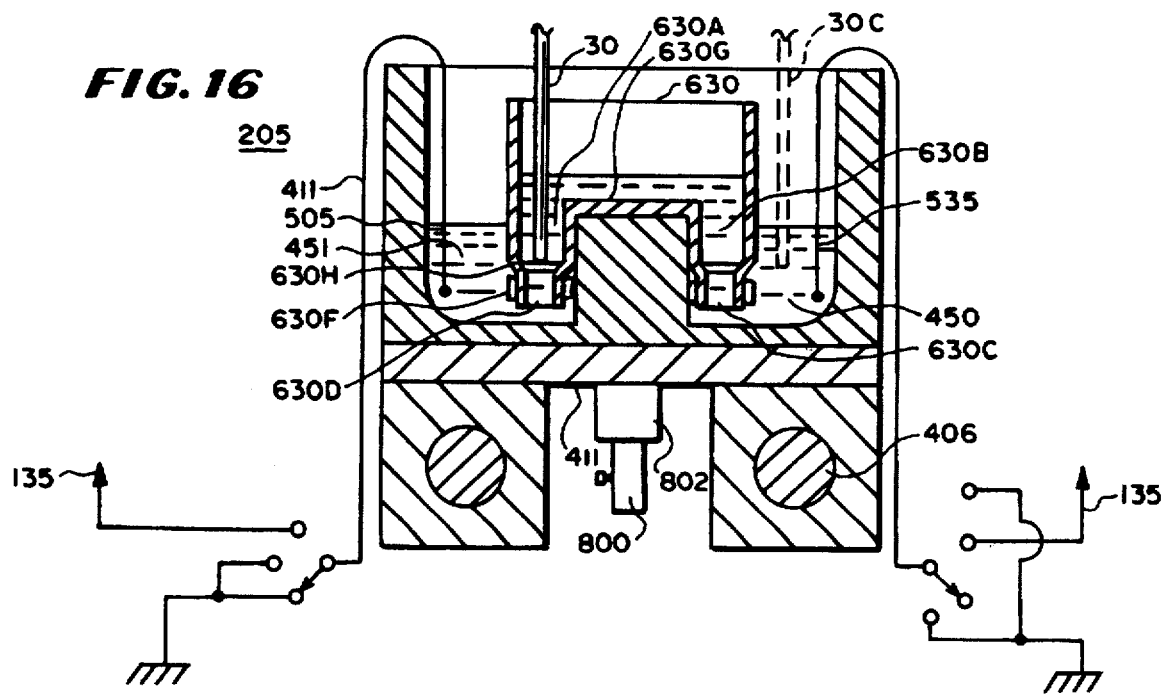
FIG. 16 is a fragmentary schematic sectional view of another embodiment of sample collecting and concentrating cup altered to include a novel salt trap for fraction collection.

In FIG. 16, there is shown a salt trap 205 that is easy to use for any common application and is particularly adaptable to be used as part of the fraction collector system 21 (FIG. 1). It eliminates the need for hydrostatic equilibrium to maintain the position of the concentrated salt "trapping solution".

In this embodiment, the fraction collector includes the capillary electrophoresis tube 30 and a salt trap composed of elements at well 630A, a well 630B, a semipermeable membrane 630C, a semipermeable membrane 630D, a narrow bore 630F, a bridge 630G and a cone bottom 630H. The membrane assembly 630D is composed and assembled similarly to the assembly 430D in FIG. 9. The semipermeable membrane (e.g. cellophane) in membrane assembly 630D supports a concentrated salt solution (dark shading) in narrow bore 630F. This salt solution does not fill the bore. An example of such concentrated solution is 7 molar ammonium acetate.

Above bore 630F is well 630A with cone bottom 630H which contains dilute buffer solution, which is the same as in the capillary tube, e.g. 0.01 molar tris acetate buffer. Because the upper, dilute solution is less dense than the lower, concentrated solution; the upper solution stably floats above the lower solution.

Since the lower solution does not fill the bore 630F, it does not diffuse significantly into the lighter solution in well 630A. During fraction collection, a sample zone of interest is eluted or discharged from capillary tube 30 into the dilute buffer solution in well 630A. Fraction collection occurs in a manner similar to that indicated in regard to FIGS. 7 and 8, except that the "waste" position is with the capillary tube 30 immersed in electrolyte 450 instead of electrolyte 451.

Advantageously, the solution in well 630A is the same composition and concentration as the buffer electrolyte in the capillary tube 30. The solution in well 630B can be the same as in well 630A. The electrolyte solution 450 in carrier 411 advantageously is the same as in capillary tube 30. The electrolyte solution 450 in carrier 411 should be the same as the electrolyte solution in capillary tube 30, because in the capillary tube waste position 30C, the capillary tube is immersed in the electrolyte solution 450.

The electrolyte solution 451 in carrier 411 should be the same as the concentrated solution in the bore 630F. This prevents diffusion across the semipermeable membrane at the bottom of the bore 630F. If electrolyte solution 451 were less concentrated, diffusion would decrease the salt concentration above the membrane at the bottom of the bore 630F. Such salt diffusion would decrease the effectiveness of the salt trap, especially as the resultant decreased density of the solution above the membrane can cause hydrostatic instability due to the production of a negative density gradient in the bore 630F.

Figure 17:
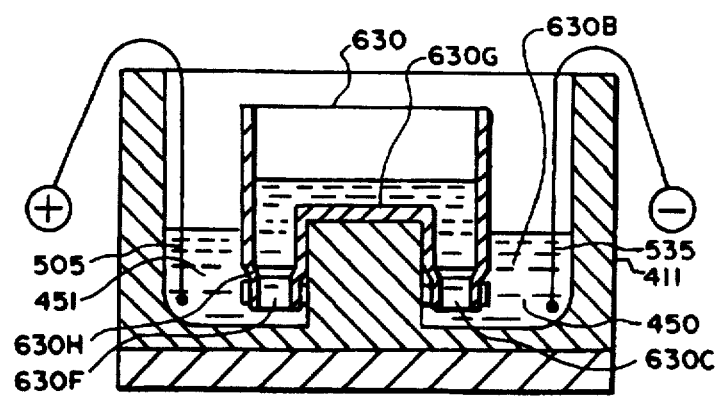
FIG. 17 is a fragmentary schematic sectional view of another embodiment of sample collecting and concentrating cup as connected for the reconcentration of samples in a novel salt trap after the initial fractionation process.

In FIG. 17, there is shown a concentration of sample into the salt trap 205 (FIG. 16) after fraction collection into buffer in well 630A (FIG. 16). Operation proceeds similarly to that described for FIG. 15. The electrolyte level in the cup 630 is raised to level 630E above bridge 630G to provide electrical continuity. This electrolyte should have the same composition as the electrolyte in wells 630A and 630B (FIG. 15). The polarity of the voltage applied to the electrodes is shown reversed from FIG. 15, as DNA is usually negatively charged.

Alternatively, concentration may be effected by using switch 201A–201B which is shown in FIG. 16 as well as FIG. 8. This switch may be used to introduce the potential difference between electrolyte buffers 451 and 450. This allows concentration of the sample without removal of carrier 411 from the apparatus of FIG. 1. It also permits filling the sample cup 630 above the bridge 630G while electrophoresis.

In operation, the separated sample (DNA or other material) migrates from well 630A (FIG. 16) and is guided by cone bottom 630H down into the concentrated salt solution in bore 630F, where it is trapped similarly in principle to that in the known "U" tube salt trap. It is trapped before reaching the semipermeable membrane in assembly 630D, so it can neither adhere to, nor pass through the membrane. The sample and trapping solution in bore 630F can be removed later with a micropipette. It is advisable to remove the cup 630 from the carrier 411 and place it on a firm surface to avoid puncturing the membrane with the micropipette. After this operation, the sample may be treated in any way similar to that for sample removal from concentrated salt solution which has resided in a conventional salt trap. Ethanol precipitation of DNA is an example of such treatment.

Another trapping technique useful for the purposes of this invention is solid phase extraction. It may be particularly useful in micellular capillary electrophoresis. In solid phase extraction, a particulate packed bed traps analate from its solution. The bed material is chosen so that it interacts with the analate more strongly than the solvent interacts with the analate. Also, the bed material should interact weakly with the solvent in which the analate is dissolved or suspended.

Because of these interactions, the analate is removed from the solvent and becomes trapped on the surface of the bed particles. The concentrated analate is eluted later from the bed particles with a second solvent which interacts strongly with both the bed material and the analate. Preferably, the second solvent should be miscible with the original solvent and readily displace the first solvent from pores in the particles of bed material. Many types of bed material are useful.

A material consisting of $C_{18}$ hydrocarbon bonded to porous silica particles has wide application. The particles may be on the order of 100 micrometers in diameters. The solid phase extraction trapping technique is well known. An example of a review article on this topic is G. A. Junk, "Synthetic Polymers for Accumulating Organic Compounds from Water", *Organic Pollutants in Water . . . Sampling, Analysis, and Toxicity Testing*, American Chemical Society Advances in Chemistry Series, 214 (1984). Solid phase extraction devices for liquid chromatography sample cleanup are well-known and are commercially available from a number of suppliers, for example, the Bond Elut® units available from Analytichem International Inc., Harbor City, Calif. These units are available with a large variety of packing bed materials for various applications.

Figure 18:
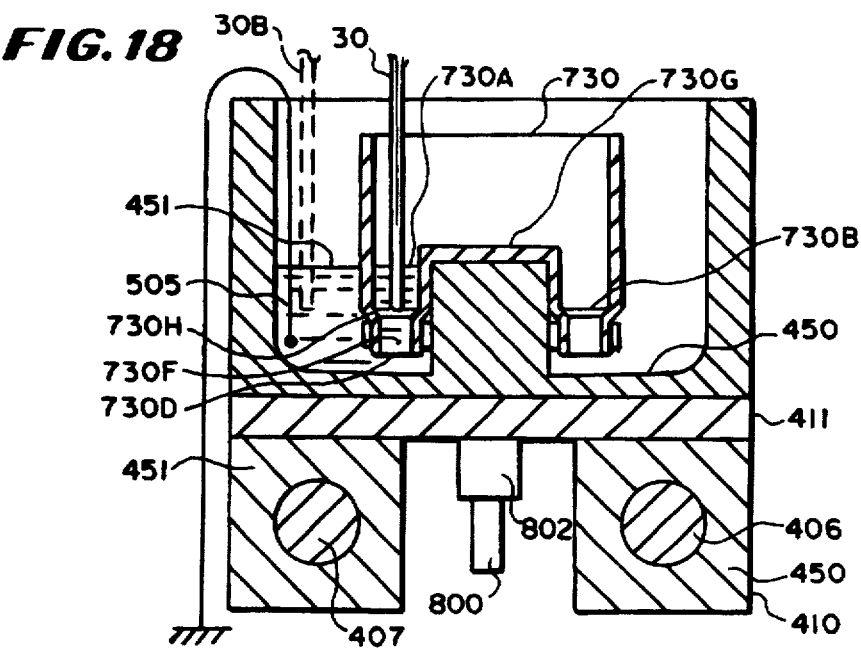
FIG. 18 is a fragmentary schematic sectional view of another embodiment of sample collecting and concentrating cup that is a part of FIG. 7, altered to include solid phase extraction for fraction collection.

In FIG. 18, there is shown a sectional view of a fraction collector using a solid phase extraction trap, having a cup 730 and a carrier 411. The amount of buffer 450, if any, is insignificant in amount and does not reach any part of cup 730. Separated analate leaves capillary tube 30 and goes into the buffer in well 730A, with electrical continuity, provided by the path through particulate bed 730F, membrane filter assembly 730D, buffer electrolyte 451 and grounded electrode 505.

A membrane filter is used in assembly 730D instead of a semi-permeable membrane. The membrane filter in assembly 730D has relatively large pores, just small enough to prevent the particles in the bed 730F from passing through it. It provides easy passage for liquid as well as ions. During periods between fraction collection, the capillary moves to position 30B and discharges waste materials into electrolyte 451.

After fraction collection, the separated analate in well 730A is first trapped in, and then eluted from the particulate packing bed 730F as follows: (1) the cup 730 is removed from the carrier 411; (2) upon removal, the buffer containing the separated analate in the well 730A is funneled by conical surface 730H into the particulate bed 730F; (3) the buffer flows through the bed 730F, passes through the membrane filter at 730D; and drips to waste from the bottom surface of the filter. However, the separated analate is trapped on the surface of the particles in the bed.

Figure 19:
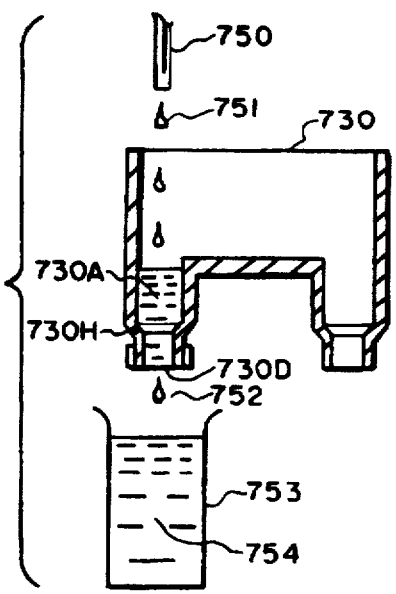
FIG. 19 is a fragmentary schematic sectional view of another embodiment of sample collecting and concentrating cup as connected for the elution of trapped sample from the solid phase extraction.

In FIG. 19, there is shown a diagrammatic drawing of a solid phase trap in which the buffer is held in the bed by the viscious friction forces due to its passage through the bed and may be flushed from the bed by refilling the well 730A with distilled water from a pipette 750. This wash water goes to waste and it is not necessary to collect it as it drops (752) from the membrane filter at 730D. The trapped analate is then eluted from the bed with an appropriate second solvent as indicated earlier. Methanol or acetonitrite solutions are examples of eluting solvents that are useful for certain applications with a $C_{18}$ bonded phase particle bed. The eluting solvent is pipetted (750) into well 730A, where it removes the analate from the bed, passes through the membrane at 730D carrying the analate with it, and drips into receiving vessel 753. Preferably, the eluting solvent is volatile enough so that the contents 754 can easily be evaporated to provid a concentrated analate.

In FIG. 20, there is shown an elevational view of the carrier 411, plate 410, a pinion 800 and the vacuum vessel assembly 80 mounted together with the pinion 800 positioned to drive the plate 410 together with the removable carrier 411 and the fixed vacuum vessel assembly 80.

The vacuum vessel assembly 80 includes an electrode buffer vessel 96 mounted to the plate 410 and the removable cap 98 connected by hoses to a source of vacuum as described above and adapted to apply vacuum pressure to the capillary tube 30 (FIG. 1) for the purpose of sample injection.

The plate 410 supports the carrier 411 which may be removed for concentrating effluent within it or replaced to continue operations while the concentration is going on or for any other reason. They are all driven together by the pinion 800 which engages the rack 802 in the center of the plate 410 to incrementally, one cell at a time, move the carrier 411 over the capillary tube 30 so that it may be inserted into buffer solution therein for removal of either waste or for extraction of separated molecular species.

Before operating the capillary electrophoresis apparatus, the capillary tube 30 (FIG. 1) should be arranged as shown in FIG. 1. Samples to be separated should be placed in sample tubes on sample holding reel 44 (FIG. 1). Electrolyte buffers suitable for the separation are placed in electrolyte vessels 60A, 60B, 60C and 96 (FIG. 1). Sample concentrating cells are placed in the carrier 411, buffer added and the carrier 411 loaded on the plate 410 at the first collection position.

The apparatus is preferably operated under the control of a conventional programmed controller or computer but may be operated by hand. In operation, if the proper buffer electrolyte is not already in the capillary tube 30 (FIG. 1), the movable arm 46 (FIG. 1) puts the end of the capillary tube 30 in the desired buffer vessel 60A, 60B or 60C (FIG. 1) and an external control signal on conductor 116 (FIG. 1) activates pressure control solenoid valve 88 (FIG. 1) putting a partial vacuum in the buffer reservoir by connecting it through tubes 94 (FIG. 1) and 114 (FIG. 1) to low-pressure vacuum tank 84 (FIG. 1). This pulls buffer from vessel 60A, 60B or 60C (FIG. 1) into the capillary tube 30, and into vessel 96 (FIG. 1), completely filling the capillary tube 30. Advantageously, the pressure sensor 80A (FIG. 1) should be part of a programmable system so that different degrees of reduced pressure or partial vacuum may be preset in the tank by the external computer 119 (FIG. 1).

It is desirable that a higher vacuum be used to rapidly fill the tube and a lower vacuum be used to more slowly pick up a minute amount of sample. A typical higher vacuum is 500 centimeters of water or about one-half of an atmosphere. A typical lower vacuum is 30 centimeters of water. When it is desired to effect a separation, the vertical section of the capillary tube 30 dips into a sample tube such as 58A (FIG. 1) or 58B (FIG. 1) on sample holding reel 44 (FIG. 1). A minute amount of sample is withdrawn into the capillary tube 30 by the application of negative pressure on electrode buffer vessel 96.

When pressure control solenoid valve 88 (FIG. 1) operates to reduce the pressure in electrode buffer vessel 96, the pressure does not reduce instantaneously. The finite rate of pressure reduction along with variations in the vacuum in tank 84 (FIG. 1) can cause an error in the sample volume. When pressure control solenoid valve 88 is released to electrode buffer vessel 96 and raise its pressure to atmospheric pressure, the pressure does not rise instantaneously. The finite rate of pressure rise can also cause an error. Since the bore of the capillary tube 30 is very small, under 100 micrometers, the flow induced by pressure differences of less than one atmosphere results in laminar flow; flow of a rate which is proportional to the pressure (transitional and turbulent flow result in flow rates that are not directly proportional to pressure). The volume of sample taken up therefore is proportional to the time integral of the flow rate.

Since flow rate is proportional to pressure, the volume of the sample is therefore also proportional to the time integral of the negative gauge pressure within the electrode buffer vessel 96. Pressure sensor 80A (FIG. 1) monitors the negative gauge pressure within electrode buffer vessel 96 and transmits it through electrical cable 92 (FIG. 1) to electrical interface 82 (FIG. 1) and thence to an external controller or computer through lead 106. For accuracy, this requires that the viscosity of the liquid in the capillary tube 30 remain constant. This is ensured by the temperature control arrangements discussed earlier.

In a first embodiment, the computer serving as a high pressure control module 121 operates the pressure control solenoid valve 88 for a fixed time to reduce the pressure in vessel 96 while accumulating the integral of the reduced pressure and thereby tabulates sample volumes for display or corrects chromatographic peak data. Peak data are corrected by dividing them by an amount proportional to the integral of reduced pressure. Any convenient proportionality factor may be chosen but it must be the same for all samples to be compared. Examples of the peak data that are corrected are all data points from the detector signal or data corresponding to the height or area of each peak of interest. This correction provides a more accurate representation of the amount of sample in each electrophoresis or chromatographic peak or the amount eluted.

In a second embodiment, the controller operates the pressure control solenoid valve 88 to pick up sample and simultaneously monitors the accumulating integral. When the integral reaches a preset value, the controller de-energizes the solenoid valve 88. This has been found to provide very reproducible sample pickups that correspond to a predetermined amount even though the finite rate of pressure rise after injection is not compensated. This embodiment has the advantages that the sample volume may be preset on the controller in terms of real pressure multiplied by time units, such as kiloPascal-seconds (units proportional to volume of sample, which are the integral of pressure with respect to time).

A third embodiment is a refinement of the second embodiment. It requires picking up a calibrating or "dummy" sample in the same manner as in the second embodiment. In this case, the controller measures the accumulating integral and de-energizes the valve 88 upon reaching the preset value of the integral, but also measures the final value of the integral upon pressure equilibrium after the valve 88 is de-energized. This final value of integral is attained when electrode buffer vessel 96 reaches equilibrium at atmospheric pressure. The difference between the preset integral and the final value of the integral represents an error that is corrected by subtracting this error from the preset value to form a corrected preset value. Actual sample pickups are then made using the second embodiment with the corrected preset value. These samples accurately correspond to a predetermined amount.

The third embodiment may be carried further, with the controller being programmed as follows to iteratively determine the proper energization time of pressure control solenoid valve 88 to cause the sample to correspond to a predetermined amount: as before, the final integral of reduced pressure in the electrode buffer vessel 96, which corresponds to either an actual or a dummy sample injection, is accumulated. All further samples are actual samples. Using the same method, the controller calculates a new corrected value for the next sample injection so that the sample volume for the second sample injection is correct, and so on for further samples, so that further sample volumes do not drift in amount.

The preferred embodiment is a combination of the first embodiment and the second embodiment. When the controller operates the valve 88, a first vacuum pressure integral is accumulated and the controller shuts the valve 88 and terminates the first integral when a preset value of integral is reached, as in the second embodiment. Although shutting the solenoid valve 88 vents tubing 94 and the vessel 96 to atmosphere at this time, the vacuum pressure does not decay immediately. Variations in this decay can cause an error.

In the preferred embodiment, this error is corrected by accumulating a second vacuum pressure integral after the valve 88 is shut for a period of time sufficient for the pressure in the tube 94 and the vessel 96 to reach atmospheric pressure. A period of one second is more than adequate. The peak data are then corrected, first by multiplying them by the first integral and then dividing them by the sum of the first integral plus the second integral. This provides the theoretically perfect numeric correction of the first embodiment while keeping the actual injected volume more repeatably controlled as in the second embodiment.

After a sample is taken up into the end of the capillary tube 30 (only a very small amount of sample is taken up, often on the order of a nanoliter), movable arm 46 (FIG. 1) moves the end of the capillary tube 30 into one of the buffer vessels 60A, 60B or 60C (FIG. 1). The high voltage power supply 14 (FIG. 1) is turned on, preferably also by automatic means, the electrode manifold 301 is operated to apply potential and the fraction collector starts in the waste position. The sample starts to migrate and separate in the capillary tube 30 in response to the potential across the capillary tube.

Figure 21:
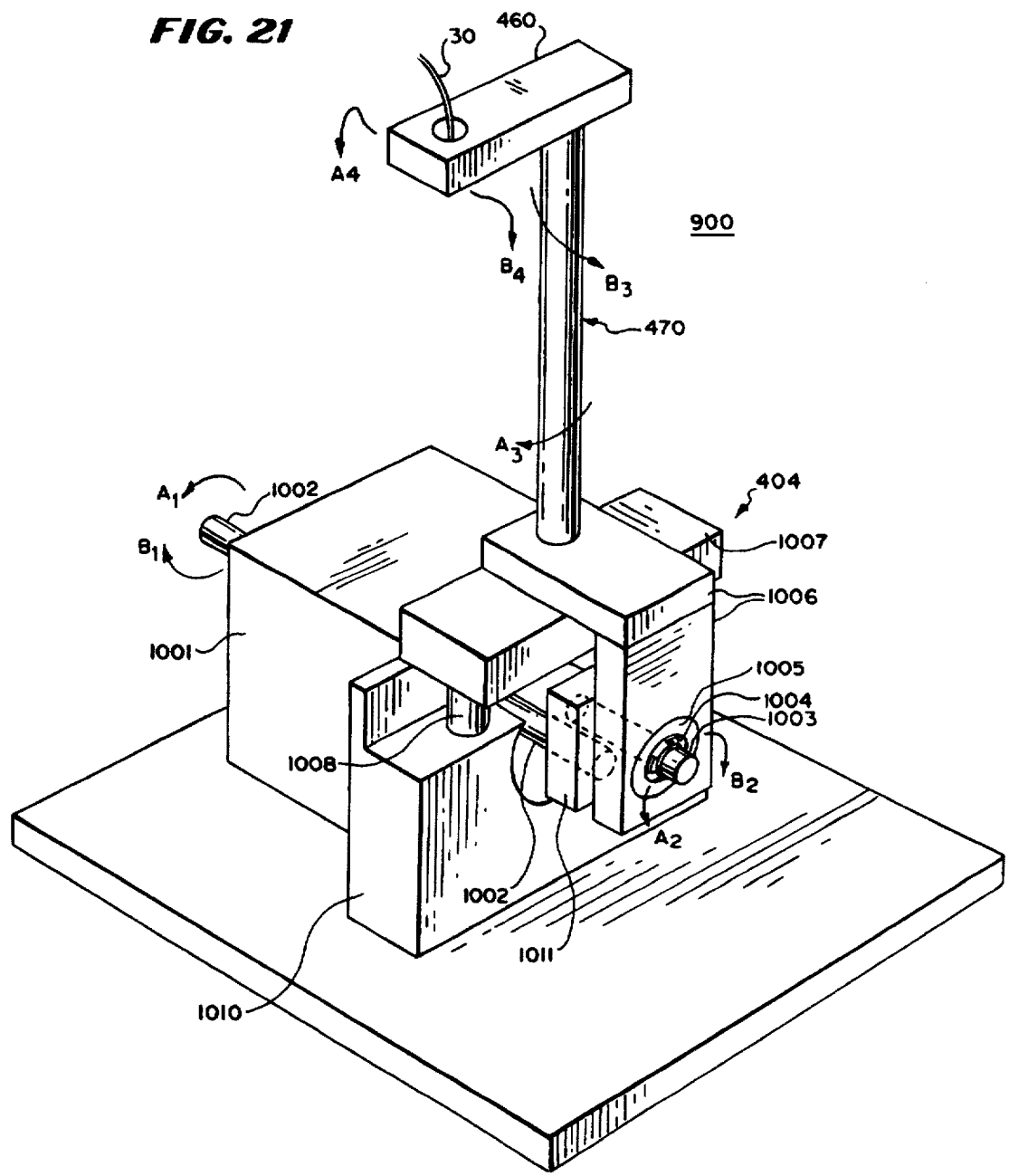
FIG. 21 is an isometric view of a portion of the fraction collector of FIG. 1.

In FIG. 21, there is shown a perspective view of the lifting and rotating rod assembly 900 having the lifting and rotating mechanism 404 for moving the lifting and rotating rod 470 vertically and rotating it for the purpose of positioning the capillary tube 30 (FIG. 1). The lifting and rotating rod assembly 900 is composed of lifting and rotating rod 470, and lifting and rotating mechanism 404 which includes a stepping motor 1001 with shaft 1002, crank arm 1011, crank rod 1003, bearing 1004 with a spherical outside diameter and a cylindrical hole to receive the crank rod 1003 with a slip fit to allow relative rotating and sliding motion between the rod and the hole, bearing retainer 1005 with spherical recess for retaining the bearing 1004, operating arm 1006 rigidly fastened to rod 470, support block 1010 supported by guide rods 1008 and 1009 (not visible on FIG. 21) which slide in support block 1010.

The spherical recess in bearing retainer 1005 retains the bearing 1004 with close spherical contact. Spherical bearing 1004 is free to wobble rotatively at any angle within the retainer 1004, but it cannot move translatively within retainer 1004.

The arm 460 is shown in its uppermost position in FIG. 21, halfway between the two downmost positions. It can be seen that if motor shaft 1002 rotates in direction A1, the crank rod 1003 moves in direction A2, the bearing 1004 swings to the left and down, the lifting and rotating rod 470 rotates and lowers in direction A3 and the end of the arm 460 which bears the capillary tube 30 swings to the rear and downward shown as A4.

If the motor shaft rotates in direction B1, rod 1003 moves in direction B2. The bearing 1004 swings to the right and down, rod 470 rotates and lowers in direction B3 and arm 460 moves capillary tube 30 in the direction B4. It has been found that good capillary positioning action results when the shaft 1002 of the stepping motor 1001 is stepped about 120 degrees in each direction from high center. This is a total rotation of 240 degrees from one full-down position of the capillary to the other full-down position.

In FIG. 22, there is shown a block diagram of fluid and electrical circuitry used to draw samples having the pressure vessel 80, the liquid trap 503, the sample injection system 16, the absorbance monitor 70 and a recorder and display apparatus 1002. The pressure vessel 80 accommodates the end of the capillary tube 30 (FIG. 1) during sample injection and during the filling of the capillary tube 30 with buffer. For this purpose, the sample injection system 16 is electrically connected to the absorbance monitor 70 to provide corrections to chromatographic data and to the pressure vessel 80 to create the appropriate vacuum pressure for drawing buffer or sample through the liquid trap 503. The sample injection system 16 is also connected to the recorder and display 1002 for displaying corrected graphs and displaying the same.

To create the appropriate vacuum pressure and correct graphs, the sample injection system 16 includes a pneumatic section 1004 and an electrical section 1006 electrically connected to an output from the absorbance monitor 70 and to the recorder and display 1002. The pneumatic section 1004 communicates with the liquid trap 503 and with the electrical system to apply pressure through the liquid trap 503 and conduit 94 to the pressure vessel 80 and to measure the amount of sample introduced as a function of the integral of vacuum pressure.

To generate vacuum pressure under the control of the electrical section 1006, the pneumatic section 1004 includes the pressure sensor 80A, the pneumatic valve 88, the pressure tank 84 and pneumatic pump 86. The pneumatic pump 86 is controlled by the electrical section 1006, which electrical section 1006 receives signals representing the pressure in the pressure tank 84 from a sensor 128 and in accordance therewith controls the vacuum pressure in the pressure tank 84. The pressure tank 84 communicates through a conduit 114 with the valve 108 which responds to the electrical system to apply negative vacuum pressure to the pressure vessel 80 or to vent it to air in the appropriate time sequence. The pressure sensor 80A applies signals to the electrical section 1006 to aid in the determination of the vacuum conditions and to generate signals which may be used to measure the amount of sample introduced in the capillary tube 30 (FIG. 1).

To increase the accuracy of the graphs by measuring the amount of sample introduced or increasing the accuracy of a predetermined amount of sample to be introduced, the electrical section 1006 includes the electrical interface 82, a high pressure control module 121, a low pressure control module 118 which includes a pressure integrator, a peak curve module 1010, and a sequence module 1012. The electrical interface 82 is electrically connected to the pressure sensor 80A to receive signals therefrom and apply them to the low pressure control module 118 and the high pressure control module 121. The low pressure control module 118 includes an integrator. The high pressure module 121 in addition to receiving signals from the sensor 128 and controlling the pneumatic pump 86 may also receive signals from the sequence module 1012 to which it is connected. The sequence module 1012 contains the preset pressure integral information. The low pressure control module 118 also receives signals from the sequence module 1012 to permit the application of a controlled amount of vacuum pressure at specific preset times in some embodiments. The output of the low pressure control module 118 controls the pneumatic valve 88 for the same purpose as well as sequence signals.

The peak curve module 1010 in conjunction with the pressure integrator in control module 118 corrects the data from the absorbance monitor 70 by a factor proportional to the integral of pressure with respect to time. This pressure is obtained from pressure sensor 80A and interface 82 and may be measured for an amount of time determined by sequence module 1012. The sequence module 1012 is connected to the peak curve module 1010 and to the pressure integrator in module 118 so that an excess integral of pressure may be subtracted from the preset measure integral value stored in the sequence module 1012. Alternatively, the peak curve module 1010 can receive the integral of pressure for a final time at which time the pressure from the pressure vessel 80 reaches atmospheric pressure and divide it into the preset pressure integral at which the pneumatic valve 88 vents to air under control of the low pressure control module 188 to provide a proportionality factor by which the electrophoresis or chromatographic data is multiplied.

This proportionality factor is the ratio of the integral of the pressure until switching of the pneumatic valve 88 to the integral of the pressure over the total time period. The peak curve module 1010 also is a means for interactively repeating the correction on successive sample injection to apply repeated correction factors to the measured data to correct for ongoing variations in the time during which the vacuum pressure is changing.

From the above description, it can be understood that the sample injection apparatus of this invention has the advantage of providing a high degree of sample introduction accuracy because of integration of the vacuum level during sample injection.

Although a preferred embodiment of the invention has been described with some particularity, many modifications and variations are possible in the preferred embodiment in the light of the above teachings. Therefore, it is to be understood that, within the scope of the appended claims, the invention may be practiced other than as specifically described.

What is claimed is:

1. A sample injector for injecting sample into a separating means in a separating apparatus, comprising:

means for applying a controlled pressure to said separating means;

said means for applying a controlled pressure including a pressure chamber;

said pressure chamber communicating with a first end of the separating means to impart a pressure difference with respect to a second end of said separating means;

said second end of the separating means being adapted to communicate with a sample source;

means for causing pressure in said pressure chamber to inject sample from said sample source wherein sample flows at a slow rate into said second end of the separating means; and pressure measuring means adapted to measure the pressure in said pressure chamber and generate a pressure signal indicative thereof; and means for determining a measure of the amount of sample introduced into said separating means from said pressure signal.

2. A sample injector according to claim 1 further including means for causing an increase in the accuracy of quantative results obtained from said sample in response to said signal.

3. Apparatus according to claim 2 in which said means for applying a controlled pressure includes means for causing the flow in said separating means to be proportional to said pressure difference in said separating means and said means for determining a measure of the amount of sample introduced includes integrating means for integrating said pressure differences with respect to time to provide an integral signal.

4. Apparatus according to claim 3 in which said means for causing an increase in the accurancy includes correction means for correcting measured quantative data, said correction means includes means for causing the pressure difference applied to the separating means to be applied for a predetermined time, and means for adjusting data by a factor substantially proportional to said integral signal.

5. Apparatus according to claim 4 in which said separating means is a capillary electrophoresis means with a capillary tube having an inside diameter between 5 and 500 micrometers and a length between 5 and 500 centimeters.

6. Apparatus according to claim 5 including means for determining a final value of the integral and wherein the means for adjusting data incorporates division of the data by the final value of the integral.

7. Apparatus according to claim 4 including means for determining a final value of the integral and wherein the means for adjusting data incorporates division of the data by the final value of the integral.

8. Apparatus according to claim 3 including correction means which includes means for applying vacuum pressure until the integral signal reaches a predetermined amount whereby a preset amount of sample is introduced.

9. Apparatus according to claim 8 in which said correction means includes means for applying vacuum pressure until a predetermined amount of sample has been introduced and means for adjusting separation data by a factor substantially proportional to the integral signal.

10. Apparatus according to claim 9 in which said separating means is a capillary electrophoresis means with a capillary tube having an inside diameter between 5 and 500 micrometers and a length between 5 and 500 centimeters.

11. Apparatus according to claim 10 including means for determining a final value of the integral and wherein the means for adjusting data incorporates division of the data by the final value of the integral.

12. Apparatus according to claim 9 including means for determining a final value of the integral and wherein the means for adjusting data incorporates division of the data by the final value of the integral.

13. Apparatus according to claim 8 in which said correction means includes means for applying vacuum pressure until a predetermined amount of sample has been introduced, means for adjusting the predetermined integral by a factor substantially proportional to the integral signal; using the new predetermined value of integral for the next injection and measuring the error for a still further corrected value, whereas the precision of injection corrects for changes in vacuum system characteristics.

14. Apparatus according to claim 13 in which said correction means further includes means for repeating the determination of a calibration factor and correction of peaks using the calibration factor.

15. Apparatus according to claim 14 in which said separating means is a capillary electrophoresis means with a capillary tube having an inside diameter between 5 and 500 micrometers and a length between 5 and 500 centimeters.

16. Apparatus according to claim 13 in which said separating means is a capillary electrophoresis means with a capillary tube having an inside diameter between 5 and 500 micrometers and a length between 5 and 500 centimeters.

17. Apparatus according to claim 8 in which said separating means is a capillary electrophoresis means with a capillary tube having an inside diameter between 5 and 500 micrometers and a length between 5 and 500 centimeters.

18. Apparatus according to claim 2 in which said separating means is a capillary electrophoresis means with a capillary tube having an inside diameter between 5 and 500 micrometers and a length between 5 and 500 centimeters.

19. A sample injector for injecting sample into a separating means in a separating apparatus, comprising:

said sample injector including a vacuum source;

a sample source and a vacuum chamber;

said vacuum chamber communicating with an end of an elongated separating means;

said separating means having a second end which communicates with the sample source;

means for causing vacuum in said vacuum chamber to draw sample from said sample source, wherein sample is pulled at a slow rate into said second end of the separating means; and pressure measuring means adapted to measure negative pressure in said vaccum chamber and generate a signal indicative thereof;

said signal causing a connective means to increase the accuracy of quantative results obtained from said sample.

20. Apparatus according to claim 19 in which the rate of the said drawing of sample in the said separating means is proportional to the said negative pressure in the said vacuum chamber and in which the said connective means incorporates correction means which integrates the said negative pressure with respect to time.

21. Apparatus according to claim 20 in which said means for causing an increase in the accurancy includes correction means for correcting measured quantative data, said correction means includes means for causing the pressure difference applied to the separating means to be lowered for a predetermined time, and means for adjusting data by a factor substantially proportional to said integral signal.

22. Apparatus according to claim 21 including means for determining a final value of the integral and wherein the means for adjusting data incorporates division of the data by the final value of the integral.

23. Apparatus according to claim 20 in which said correction means includes means for applying vacuum pressure until the integral signal reaches a predetermined amount whereby a preset amount of sample is introduced.

24. Apparatus according to claim 23 in which said correction means includes means for applying vacuum pressure until a predetermined amount of sample has been introduced and means for adjusting data by a factor substantially proportional to the integral signal.

25. Apparatus according to claim 24 including means for determining a final value of the integral and wherein the means for adjusting data incorporates division of the data by the final value of the integral.

26. Apparatus according to claim 23 in which said correction means includes means for applying vacuum pressure until a predetermined amount of sample has been introduced, means for adjusting the predetermined integral by a factor substantially proportional to the integral signal; using the new predetermined integral for the next injection and measuring the error for a still further corrected value, whereas the precision of injection corrects for changes in vacuum system characteristics.

27. Apparatus according to claim 26 in which said correction means further includes means for repeating the determination of a calibration factor and correction of peaks using the calibration factor.

28. Apparatus according to claim 27 in which said separating means is a capillary electrophoresis means with a capillary tube having an inside diameter between 5 and 500 micrometers and a length between 5 and 500 centimeters.

29. A method of injecting sample into a separating means in a separating apparatus, comprising the steps of:

applying a controlled pressure to said separating means from a pressure chamber that communicates with a first end of the separating means to impart a pressure difference with respect to a second end of said separating means adapted to communicate with a sample source;

causing pressure in said pressure chamber to inject sample from said sample source wherein sample flows at a slow rate into said second end of the separating means;

measuring the pressure in said pressure chamber;

generating a pressure signal indicative of the pressure in said presure chamber; and determining a measure of the amount of sample introduced into said separating means from said pressure signal.

30. A method according to claim 29 further including the step of causing an increase in the accuracy of quantative results obtained from said sample in response to said signal.

31. A method according to claim 30 in which the step of applying a controlled pressure includes the step of causing the flow in said separating means to be proportional to said pressure difference in said separating means and said step of determining a measure of the amount of sample introduced includes the step of integrating said pressure differences with respect to time to provide an integral signal.

32. A method according to claim 31 including the step of applying pressure until the integral signal reaches a predetermined amount whereby a preset amount of sample is introduced.

33. A method according to claim 32 in which the step of correcting includes the steps of applying pressure until a predetermined amount of sample has been introduced and adjusting separation data by a factor substantially proportional to the integral signal.

34. A method according to claim 33 including the steps of determining a final value of the integral and dividing the data by the final value of the integral.

35. A method according to claim 32 in which the steps of correcting includes the steps of applying pressure until a predetermined amount of sample has been introduced; adjusting the predetermined integral by a factor substantially proportional to the integral signal; using the new predetermined value of integral for the next injection and measuring the error for a still further corrected value, whereas the precision of injection corrects for changes in vacuum system characteristics.

36. A method according to claim 35 in which the step of correcting further includes the steps of repeating the determination of a calibration factor and the correction of peaks using the calibration factor.

37. A method according to claim 30 in which the step of causing an increase in accuracy includes the steps of applying pressure for a predetermined time and adjusting the separation data by a factor substantially proportional to the integral signal.

38. A method according to claim 37 including the steps of determining a final value of the integral and dividing the data by the final value of the integral.

39. A method of injecting sample into a separating means in a separating apparatus, comprising the steps of:

causing a vacuum in said vacuum chamber to draw sample from said sample source, wherein sample is pulled at a slow rate into said second end of the separating means;

measuring negative pressure in said vacuum chamber;

generating a signal indicative of the negative pressure to cause a connective means to increase the accuracy of quantative results obtained from said sample;

the step of drawing sample including the step of drawing sample into said separating means proportionally to the said negative pressure in the said vacuum chamber and integrating the negative pressure with respect to time.

40. A method according to claim 39 in which the step of causing an increase in the accuracy includes the steps of correcting measured quantative data, said step of correcting measured quantative data including the substeps of causing the pressure difference applied to the separating means to be applied for a predetermined time, and adjusting data by a factor substantially proportional to said integral signal.

41. A method according to claim 39 in which the step of causing an increase in the accuracy includes the step of applying vacuum pressure until the integral signal reaches a predetermined amount whereby a preset amount of sample is introduced.

42. A method according to claim 41 in which the step of causing an increase in the accuracy includes the steps of applying vacuum pressure until a predetermined amount of sample has been introduced and adjusting data by a factor substantially proportional to the integral signal.

43. A method according to claim 41 in which the step of causing an increase in the accuracy includes the steps of applying vacuum pressure until a predetermined amount of sample has been introduced, adjusting the predetermined integral by a factor substantially proportional to the integral signal; using the new predetermined integral for the next injection and measuring the error for a still further corrected value, whereas the precision of injection corrects for changes in vacuum system characteristics.

44. A method according to claim 43 in which the step of correcting further includes the steps of repeating the determination of a calibration factor and correcting peaks using the calibration factor.

* * * * *